United States Patent [19]
Csaky et al.

[11] Patent Number: 5,998,598
[45] Date of Patent: Dec. 7, 1999

[54] IMMUNOADHESINS AND METHODS OF PRODUCTION AND USE THEREOF

[75] Inventors: Karl G. Csaky, Kensington; Eddy Anglade, Silver Spring; Daniel M. Sullivan; William LaRochelle, both of Gaithersburg, all of Md.

[73] Assignee: The United States of America, as represented by the Department of Health and Human Services, Washington, D.C.

[21] Appl. No.: 08/814,567

[22] Filed: Mar. 10, 1997

[51] Int. Cl.$^6$ .......................... A61K 48/00; C07H 21/04; C12N 15/62; C12N 15/13

[52] U.S. Cl. ........................ 536/23.4; 435/320.1; 514/44; 536/23.1; 536/23.53; 536/23.72; 536/24.1

[58] Field of Search ........................... 435/320.1; 514/44; 536/23.4, 23.5, 23.53, 23.72, 24.1, 23.1

[56] References Cited

U.S. PATENT DOCUMENTS 5,316,921  5/1994  Godowski et al. .

FOREIGN PATENT DOCUMENTS

| 0 325 224 a3 | 7/1989 | European Pat. Off. . |
| WO 94/04690 | 3/1994 | WIPO . |
| WO 94/28938 | 12/1994 | WIPO . |
| WO 95/21258 | 8/1995 | WIPO . |

OTHER PUBLICATIONS

Aruffo et al. "CD44 is the principal cell surface receptor for hyaluronate" *Cell* 61(7), 1303–13 (1990).

Haak–Frendscho et al. "Human IgE receptor α–chain lgG chimera blocks passive cutaneous anaphylaxis reaction in vivo" *J Immunol* 151(1), 351–8 (1993).

Hannum et al. "Interleukin–1 Receptor Antagonist Activity of a Human Interleukin–1 Inhibitor" *Nature* 343:336–40 (1990).

LaRochelle et al. "Specific receptor detection by a functional keratinocyte growth factor–immunoglobulin chimera" *J Cell Biol* 129(2), 357–66 (1995).

Levrero et al. "Defective and nondefective adenovirus vectors for expressing foreign genes in vitro and in vivo" *Gene* 101(2), 195–202 (1991).

Linsley et al. "Binding of the B cell activation antigen B7 to CD28 costimulates T cell proliferation and interleukin 2 mRNA accumulation" *J Exp Med* 173(3), 721–30 (1991).

McGrory et al. "A simple technique for the rescue of early region 1 mutations into infectious human adenovirus type 5" *Virology* 163:614–617 (1988).

Sullivan et al. "Adenovirus–mediated gene transfer of ornithine aminotransferase in cultured human retinal pigment epithelium" *Invest Ophthalmol Vis Sci* 37(5), 766–74 (1996).

Yang et al. "Construction and adhesive properties of a slouble MAdCAM–1–Fc chimera expressed in a baculovirus: phylogenetic conservation of receptor–ligand interaction" *Scand. J. Immunol.* 42:235–247 (1995).

Zheng et al. "Administration of noncytolytic IL–10/Fc in murine models of liposaccharide–induced septic shock and allogeneic islet transplantation" *J. Immunol.* 154:5590–5600 (1995).

Kollis et al. "Influence of Adenoviral–Mediated Gene Transfer of a TNF Soluble Receptor on Pulmonary host Defenses" *J. Investigative Med.*, Abstract XP–002082459, 43:41a, 1995.

*Primary Examiner*—Nancy A. Johnson
*Attorney, Agent, or Firm*—Needle & Rosenberg, P.C.

[57] ABSTRACT

The invention is directed toward a compound comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin protein. The recombinant nucleic acid encoding the immunoadhesin can be within an adenovirus. The invention further provides methods for delivering an immunoadhesin to a cell or a subject comprising administering to the cell or the subject an adenovirus comprising a recombinant nucleic acid encoding an immunoadhesin; producing an immunoadhesin comprising administering to a cell an adenovirus comprising a recombinant nucleic acid encoding an immunoadhesin inserted within an adenoviral nucleic acid, whereby the cell expresses the recombinant nucleic acid encoding the immunoadhesin, thereby producing the immunoadhesin; treating an inflammatory condition in a subject comprising administering to the subject an adenovirus comprising a recombinant nucleic acid encoding an immunoadhesin inserted within an adenoviral nucleic acid or a recombinant nucleic acid encoding an immunoadhesin inserted within an adenoviral nucleic acid, whereby a cell in the subject expresses the recombinant nucleic acid encoding the immunoadhesin and produces the immunoadhesin, thereby treating the inflammatory condition or administering to the subject a recombinant nucleic acid encoding an immunoadhesin, or an immunoadhesin, wherein the immunoadhesin is selected from the group consisting of vIL-10-IgG, IL-13-IgG, LFA-IgG, IL-2ra-IgG, IL-1ra-IgG, mutant IL-4-IgG, VLA4-IgG, IL-2-IgG, TGF-$\beta$1-IgG, TGF-$\beta 1^{223,225}$-IgG, and VCAM-IgG; and methods of screening an immunoadhesin for bioactivity.

2 Claims, 3 Drawing Sheets

IMMUNOADHESINS AND METHODS OF PRODUCTION AND USE THEREOF

BACKGROUND OF THE INVENTION

1. Field of the Invention

This invention relates generally to immunoadhesins and methods utilizing immunoadhesins. Specifically, this invention relates to methods of producing immunoadhesins, methods of delivering immunoadhesins, methods of treatment using immunoadhesins, and methods of screening immunoadhesins for bioactivity using a replication-deficient adenovirus system.

2. Background Art

Immunoadhesins are antibody-like chimeric fusion proteins comprised of an immunoglobulin gamma heavy chain constant region plus another non-immunoglobulin molecule, such as a cell surface receptor, a cell-adhesion molecule, or a ligand, and are useful for research such as receptor structure-function analysis (Cheon et al., 1994; Heidaran et al., 1995), immunohistochemistry (LaRochelle et al., 1995), ligand identification (Watson et al., 1990), and receptor isolation (Beck et al., 1994) as well as clinical therapeutics (Ashkenazi et al., 1991; Byrn et al., 1990; Chamow et al., 1992; Finck et al., 1994; Jin et al., 1994; Lenschow et al., 1992; Lin et al., 1993; Linsley and Ledbetter, 1993; Wallace et al., 1994; Zheng et al., 1995). Since immunoadhesins can be constructed from a human protein sequence with a desired specificity linked to an appropriate immunoglobulin hinge and constant domain sequence, the binding specificity of interest can be achieved entirely by using human-derived components. Therefore these immunoadhesins are minimally immunogenic to a human subject and safe for therapeutic applications. For example, the immunoadhesin CD4-IgG has been used in human clinical trials. (Hodges et al. "Phase 1 Study of Recombinant Human CD4-Immunoglobulin G Therapy of Patients with AIDS and AIDS-related Complex. Antimicrob. Agents Chemother. 35:2580–6; 1991)). Additionally, since these immunoadhesins can be constructed using various binding or "active" regions, they can be designed for treating specific conditions.

For example, noninfectious ocular inflammation of presumed autoimmune etiology is estimated to cause approximately 10% of severe visual handicap (70,000 cases per year) in the U.S. These diseases cause an inflammation of the uveal tract affecting both the anterior and posterior segments of the eye, are chronic degenerative, and potentially blinding, and are collectively known as uveitis. Affected individuals range typically in age from the first to seventh decades, although the second through fourth decades are particularly susceptible. The precise pathogenic mechanisms causing this condition remain elusive. Treatment for these conditions is by necessity nonspecific and entails the use of immunosuppressive agents which provide relief but, unfortunately, can be associated with myriad systemic side adverse effects which can be life threatening. Thus, there clearly is a need for therapeutic alternatives to current treatments that are more specific and avoid such adverse effects. The administration of immunoadhesins described herein represents such a therapeutic alternative.

To date, production of immunoadhesin molecules has entailed the use of transfection of plasmid DNA in a transient fashion or by establishment of stable transfectants (Aruffo et al., 1990; LaRochelle et al., 1995; Linsley et al., 1991). The yields of immunoadhesin obtained have ranged from 0.5–4.5 mg/i following affinity chromatography on immobilized protein A in transient transfection systems (Aruffo et al., 1990; Linsley et al., 1991). Higher concentrations (30–50 mg/l) have been described following the establishment of stable transfectants in large scale production (Haak-Frendscho et al., 1993). While these methods are useful for producing immunoadhesins, they are limited by the inefficiency of transfection and the rather labor intensive nature of establishing stable transfectants (Linsley et al., 1991). This relative lack of efficiency takes on particular significance when screening multiple constructs for activity. It is necessary to produce milligram quantities of recombinant immunoadhesins for preclinical efficacy screening. Ideally, a system for production of an immunoadhesin would combine efficient, high level gene expression, appropriate assembly/post translation modification, and ease of purification.

The methods described herein disclose such a system by providing replication-defective adenovirus vectors comprising nucleic acids encoding immunoadhesins to provide an efficient means of gene transfer into a variety of cell types. Additionally, adenovirus-mediated gene transfer results in high level protein expression. This combination of facile gene transfer and high specific activity provides a rapid means of producing milligram quantities of recombinant molecules.

This inventive system shows marked improvement over other techniques in many respects. Previous techniques involve transient transfection for protein production and result in low transfection efficiencies as well as low amounts of fusion protein production. Cumbersome screening protocols make isolation of protein producing clones time consuming and difficult. In addition, the activity of the chimeric protein can be greatly affected by the production method. The chimera may have different activities based upon whether it is made in bacteria, baculovirus, or mammalian cells.

The present replication-defective adenovirus system involves a method of producing immunoadhesins which is very close to a human system and therefore minimizes undesirable characteristics of a recombinant protein molecule such as incorrect glycosylation and other post-translational protein modifications. Moreover, this system results in transductions at surprisingly much higher efficiency resulting in greater levels of protein production and simplified screening procedures. Thus, the present methods also provide a much-needed, improved, and specific immunotherapeutic method for use in treating uveitis and, in particular, in treating individuals with autoimmune diseases that avoids the adverse side effects of previous treatments.

SUMMARY OF THE INVENTION

In accordance with the purpose(s) of this invention, as embodied and broadly described herein, this invention, in one aspect, provides a compound comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin protein. The recombinant nucleic acid encoding the immunoadhesin can be within an adenovirus genome.

The invention further provides a method of delivering an immunoadhesin to a cell or a subject comprising administering to the cell or the subject an adenovirus comprising a recombinant nucleic acid encoding an immunoadhesin inserted within an adenoviral nucleic acid, whereby expression of the recombinant nucleic acid produces the immunoadhesin, thereby delivering the immunoadhesin to the cell or the subject.

The invention also provides a method of producing an immunoadhesin comprising administering to a cell an adenovirus comprising a recombinant nucleic acid encoding an immunoadhesin inserted within an adenoviral nucleic acid, whereby the cell expresses the recombinant nucleic acid encoding the immunoadhesin, thereby producing the immunoadhesin.

The invention also provides a method of treating an inflammatory condition in a subject comprising administering to the subject an adenovirus comprising a recombinant nucleic acid encoding an immunoadhesin inserted within an adenoviral nucleic acid or a recombinant nucleic acid encoding an immunoadhesin inserted within an adenoviral nucleic acid, whereby a cell in the subject expresses the recombinant nucleic acid encoding the immunoadhesin and produces the immunoadhesin, thereby treating the inflammatory condition.

The invention also provides a method of treating an inflammatory condition in a subject comprising administering to the subject a recombinant nucleic acid encoding an immunoadhesin, or an immunoadhesin, wherein the immunoadhesin is selected from the group consisting of vIL-10-IgG, IL-13-IgG, LFA-IgG, IL-2ra-IgG, IL-1ra-IgG, mutant IL-4-IgG, VLA4-IgG, IL-2-IgG, TGF-$\beta$1-IgG, TGF-$\beta1^{223, 225}$-IgG, and VCAM-IgG.

The invention also provides a method of screening an immunoadhesin for bioactivity, comprising administering to a first cell an adenovirus containing a recombinant nucleic acid encoding the immunoadhesin, wherein the first cell expresses the recombinant nucleic acid encoding the immunoadhesin and thereby produces the immunoadhesin, contacting a second cell with the immunoadhesin, and monitoring the second cell for a biological response to the immunoadhesin, thereby screening the immunoadhesin for bioactivity.

The invention also provides a method of screening an immunoadhesin for bioactivity comprising administering to a cell an adenovirus containing a recombinant nucleic acid encoding the immunoadhesin, wherein the cell expresses the recombinant nucleic acid encoding the immunoadhesin and thereby produces the immunoadhesin, and monitoring the cell for a biological response to the immunoadhesin, thereby screening the immunoadhesin for bioactivity.

DETAILED DESCRIPTION OF THE INVENTION

Figure 1:
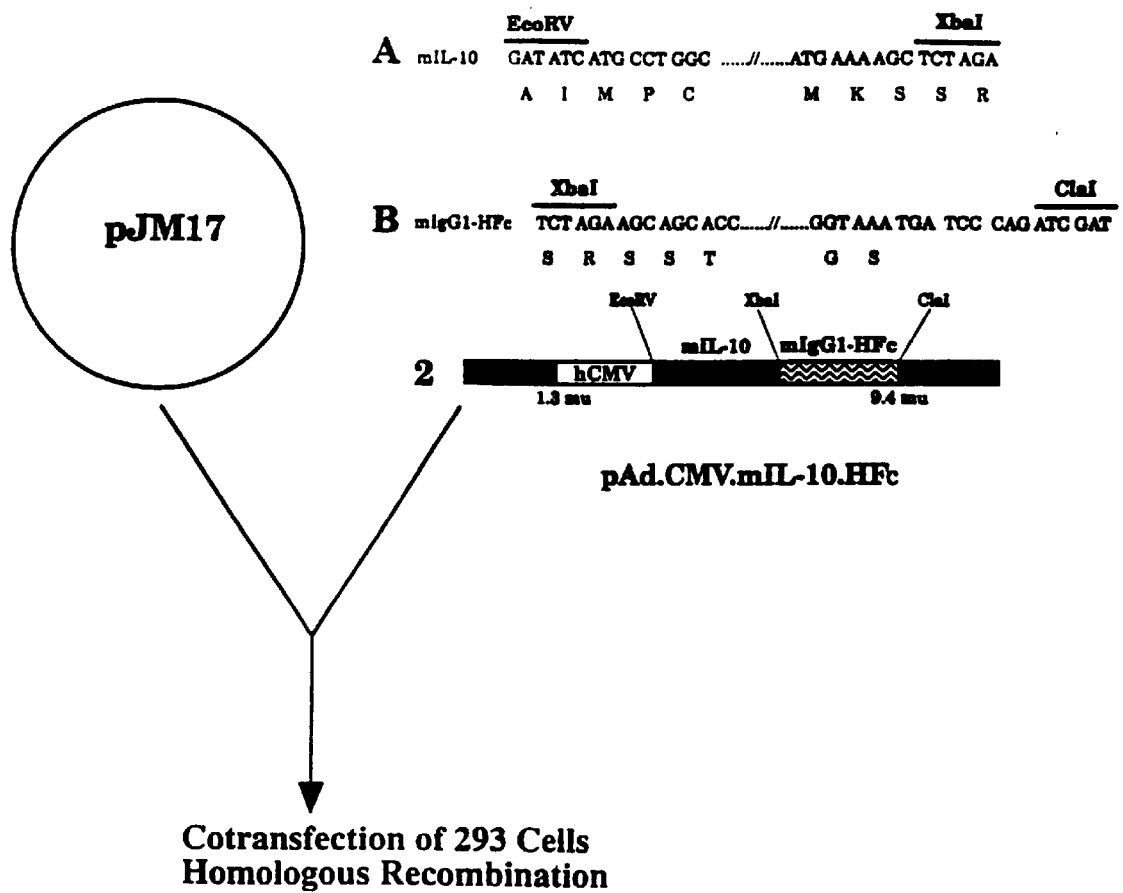
FIG. 1 shows the generation of adenoviral vector Ad5.hCMV.mIL-10:HFc. The mIL-10-encoded cDNA lacking its stop codon was recombined with the Hfc portion of the mouse immunoglobulin IgG1 heavy chain cDNA at the hinge region to form the plasmid pAd.CMV.mIL-10.HFc. The cDNA sequence and encoded amino acid residues adjacent to the cloning sites are shown (A, B). Cotransfection of 293 cells with pJM17 and pAd.CMV.mIL-10.HFc results in the generation of the adenoviral vector Ad5.hCMV.mIL-10:HFc by homologous recombination.

The present invention may be understood more readily by reference to the following detailed description of the preferred embodiments of the invention and the Examples included therein and to the Figures and their previous and following description.

It is to be understood that this invention is not limited to specific cells, specific detection methods, or specific chromosome abnormalities, as such may, of course, vary, and numerous modifications and variations therein will be apparent to those skilled in the art. It is also to be understood that the terminology used herein is for the purpose of describing particular embodiments only and is not intended to be limiting.

As used in the specification and in the claims, "a" can mean one or more, depending upon the context in which it is used. Thus, for example, reference to "a cell" means that at least one cell is utilized.

In one aspect, the invention provides a compound comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin.

Therefore, in one of its most general applications, the invention relates to a recombinant adenovirus incorporating a DNA segment having a sequence encoding an immunoadhesin. The immunoadhesin may be constructed, for example, by coupling an extracellular portion of a non-immunoglobulin molecule to an IgG heavy chain polypeptide. Typically, two immunoadhesin molecules form a homodimer. For the purposes of the invention, the term chimeric polypeptide is defined as including any polypeptide encoded by a nucleic acid where at least a portion of a nucleic acid encoding a non-immunoglobulin molecule such as a cytokine or a cytokine receptor is coupled to at least a portion of a nucleic acid encoding an immunoglobulin heavy chain polypeptide, IgG for example. The coupling may be achieved in a manner which provides for a functional transcribing and translating of the nucleic acid segment and message derived therefrom, respectively. The nucleic acid encoding the immunoadhesin is then coupled with a portion of an adenoviral nucleic acid sufficient to allow the adenoviral-immunoadhesin nucleic acid to be packaged in an adenoviral particle. The immunoadhesins of the invention may be any of a number of such immunoadhesins known in the art. An exemplary list of certain of cytokines, cytokine receptors, cellular ligands and ligand receptors is provided below for which references are specifically incorporated by reference herein for all of their teachings.

Cytokines, Cytokine Receptors, and other Examples of Cellular Ligands and Ligand Receptors Examples include, but are not limited to IL-1, IL-2, IL-3, IL-4, IL-5, IL-6, IL-7, IL-8, IL-9, IL-10, IL-12, IL-13, IL-14, IL-15, subunits of the interleukins such as IL-1α, and IL-1β; interleukin receptor antagonists such as IL-1ra and the partial agonist mutant IL-4; interferons such as IFN-α, IFN-β, IFN-γ, and IFN-ω; tumor necrosis factors such as TNF-α and TNF-β; colony stimulating factors such as the macrophage colony-stimulating factor, the granulocyte-colony stimulating factor (G-CSF) receptor Fukunaga et al., Proc. Nat. Acad. Sci. USA 87:8702–8706 (1990), and the granulocyte macrophage-colony stimulating factor (GM-CSF) receptor (beta chain) Hayashida et al., Proc. Nat. Acad. Sci. USA 87:9655–9659 (1990); transforming growth factors such as TGF-β1, very late antigen (VLA or CD29); intercellular adhesion molecule (ICAM-1 or CD54) Stauton et al., Cell 52:925–953 (1988), VCAM-1 or CD106; Human interferon gamma receptor Aguet et al., Cell 55:273–280 (1988); Human interferon alpha receptor Uze et al., Cell 60:225–234 (1990); Human Mac-1 (human complement receptor type 3) Corbi et al., J. Biol Chem. 263:12403–12411 (1988); Human insulin receptor Ebina et al., Cell 40:747–758 (1985); Human transferrin receptor McClelland et al., Cell 39:267–274 (1984); Human nerve growth factor receptor Johnson et al., Cell 47:545–554 (1986); Human leukocyte adhesion protein (beta subunit) Kishimoto et al., Cell 48:681–690 (1987); Human leukocyte adhesion receptor (alpha subunit) Arnaout et al., J. Biol. Chem. 106:2153–2158 (1988); Human interleukin-6 receptor Yamasaki et al., Science 241:825–828 (1988); Human platelet-derived growth factor (PDGF) receptor Claesson-Welsh et al., Molec. Cell. Bio. 8:3476–3486 (1988); Human insulin-like growth factor receptor Ulrich et al., EMBO J. 5:2503–2512 (1986); Human interleukin-2 receptor (beta chain); Hatakeyama et al., Science 244:551–556 (1989), Human interleukin-1 receptor Sims et al., Proc. Nat. Acad. Sci. USA 86:8946–8950 (1989); Human epidermal growth factor receptor Kraus et al., Proc. Nat. Acad. Sci. USA 86:9193–9197 (1989), Human leukocyte adhesion protein, (alpha subunit) Corbi et al., EMBO J. 6:4023–4028 (1987); Human interleukin-7 receptor Goodwin et al., Cell 60:941–951 (1990); Human vascular cell adhesion molecule-I Osborn et al., Cell 59:1203–1211 (1989); Human endothelial leukocyte adhesion molecule-1 (elam-1) Hession et al., Proc. Nat.. Acad. Sci. USA 87:1673–1677 (1990); Human prolactin receptor Boutin et al., Mol. Endocrinol. 3:1455–1461 (1989); Human thyrotropin receptor Nagayama et al., Biochem. Biophys. Res. Comm. 165:1184–1190 (1989); Human leukocyte adhesion molecule-I (lam-1) Ord et al., J. Biol. Chem. 265:7760–7767 (1990); Human basic fibroblast growth factor receptor (shorter form) Itoh et al., Biochem. Biophys. Res. Comm. 169:680–685 (1990); Human interleukin-2 receptor (TACT antigen or 55 k subunit) Leonard et al., Nature 311:626–631 (1984); Human stem cell factor receptor (c-kit) Yarden et al., EMBO J. 6:3341–3351 (1987); Human growth hormone receptor Leung et al., Nature 330:537–543 (1987); Human intercellular adhesion molecule-2 (ICAM-2 or CD 102) Staunton et al., Nature 399:61–64 (1989); Human leukocyte function associated molecule-1 (LFA-1) (alpha subunit) Larson et al., J. Cell Biol. 108:702–712 (1989); Human interleukin-4 receptor Idzerda et al., J. Exp. Med. 171:861–873 (1990); Human erythropoietin receptor Winkelmann et al., Blood 76:24–30 (1990); and Human Fas Antigen Itoh et al., Cell 66:233–243 (1991). Specific subunits of these and other molecules are also contemplated, such as mutant IL-4 (Aversa et al. "An Interleukin 4 (IL-4) Mutant Protein Inhibits both IL-4 or IL-13-induced Human Immunoglobulin G4 (IgG4) and IgE Synthesis and B Cell Proliferation: Support for a Common Component Shared by IL-4 and IL-13 Receptors" J. Exp. Med. 178:2213–8 (1993), TGF-β1 (Roberts et al. "Transforming Growth Factor Beta: Biochemistry and Roles in Embryogenesis, Tissue Repair and Remodeling, and Carcinogenesis" Recent. Prog. Horm. Res. 44:157–97 (1988), and TGF-β1$^{223,225}$ (Brunner et al. "Site-directed Mutagenesis of Cysteine Residues in the Pro Region of the Transforming Growth Factor Beta 1 Precursor. Expression and Characterization of Mutant Proteins" J. Biol. Chem. 264:13660–4 (1989). Furthermore, modifications of these molecules are contemplated such as amino acid substitutions, insertions, and deletions, for any desired purpose, such as to alter or increase the binding specificity of an immunoadhesin. Additionally, these molecules can be of non-human origin, such as other primates, murine, bovine, porcine, equine, canine, etc. In one specific embodiment, the IL-10 portion of an immunoadhesin is viral in origin (vIL-10-IgG). These examples are not limiting and are only presented for exemplary purposes. This invention provides compounds comprising a nucleic acid encoding an immunoadhesin inserted within an adenoviral nucleic acid and is therefore not limited to the specific immunoadhesin.

The nucleic acid encoding the immunoadhesin can be positioned within any location of the genome of the adenovirus wherein the adenovirus genome with this immunoadhesin insert may still be packaged into an adenovirus particle. For example, Ghosh-Choudhury et al. have indicated that the maximum amount of nucleic acid that adenovirus can package into viral capsids is approximately 2000 bases in excess of the wild-type genome. (Ghosh-Choudhury et al., (1987) EMBO J. 6:1733–1739). One can therefore position the immunoadhesin-encoding nucleic acid within or in replacement of a region of the E1 region of adenovirus, for example, to disrupt the E1 gene and therefore inactivate the cellular transforming capacity of this adenoviral gene, as well as enable the recombinant virus to express and therefore produce the desired immunoadhesin. The minimum amount of adenoviral nucleic acid in these constructs is that amount that will allow the recombinant adenoviral-immunoadhesin nucleic acid to be packaged. Additionally, the site of insertion of the nucleic acid encoding the immunoadhesin into the adenoviral genome, or portion thereof, is selected as to allow the final recombinant nucleic acid to be packaged, as is known to one skilled in the art.

The term "adenoviral genome" or "adenovirus genome" is used herein to describe an adenoviral nucleic acid that is capable of being packaged into an adenovirus particle. Therefore this nucleic acid may comprise an entire wild-type adenoviral genome or a mutant thereof, or a construct wherein the only adenoviral sequences present are those which enable the nucleic acid to be packaged into an adenovirus particle, or any variation thereof. Packagable lengths of nucleic acids for specific immunoadhesins are known in the art. This adenoviral genome can be coupled with any desired nucleic acid insert, such as an immunoadhesin, such that the adenoviral genome, when packaged into an adenovirus particle, also packages the nucleic acid insert. One skilled in the art will appreciate that the nucleic acid insert combined with the adenoviral nucleic acid will be a total nucleic acid length that will allow the total nucleic acid to be packaged into an adenovirus particle.

By "compound comprising a recombinant nucleic acid" is meant that the nucleic can be that commonly referred to as a nucleic acid, but this compound, for example, can also be a derivative of a typical nucleic acid such as nucleic acids which are modified to contain a terminal or internal reporter molecule or those nucleic acids containing non-typical bases or sugars. These reporter molecules include, but are not limited to isotopic and non-isotopic reporter molecules. Examples of non-isotopic reporter molecules include, but are not limited to biotin, LC-biotin, fluorescein, acridine, cholesterol, and dinitrophenyl labels which can be attached to a 2-aminobutyl-1,3-propanediol backbone. (Clontech, Palo Alto, Calif.).

One skilled in the art will appreciate that there are numerous techniques available by which one can obtain a nucleic acid sequence encoding an immunoadhesin. One example of a method of obtaining the nucleic acid is by constructing the nucleic acid by synthesizing a recombinant DNA molecule. For example, oligonucleotide synthesis procedures are routine in the art and oligonucleotides coding for a particular protein or regulatory region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins or regulatory regions can be synthesized by first constructing several different double-stranded molecules that code for particular regions of the protein or regulatory region, followed by ligating these DNA molecules together. For example, Cunningham, et al., "Receptor and Antibody Epitopes in Human Growth Hormone Identified by Homolog-Scanning Mutagenesis" *Science*, Vol. 243, pp. 1330–1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599–603 (1986), wherein synthesis of a 1057 base pair synthetic bovine rhodopsin gene from synthetic oligonucleotides is disclosed. Once the appropriate DNA molecule is synthesized, this DNA can be cloned downstream of an appropriate promoter. Techniques such as this are routine in the art and are well documented.

Another example of a method of obtaining an immunoadhesin is to utilize traditional recombinant techniques to generate the immunoadhesin from the native sources of the individual components. One can isolate the corresponding wild-type nucleic acid for part of the immunoadhesin from the organism in which it is found and clone it in an appropriate vector. For example, a DNA or cDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.). Once part of the immunoadhesin has been cloned, such as a cytokine, the remaining portion of the immunoadhesin, such as the immunoglobulin portion, can then be cloned adjacent to the cytokine domain in the same or in a similar manner. Once isolated, the nucleic acid encoding the immunoadhesin can be subsequently cloned into an appropriate vector, or if necessary, be modified to facilitate the subsequent cloning steps. Such modification steps are routine, an example of which is the addition of oligonucleotide linkers which contain restriction sites to the termini of the nucleic acid. Such modification steps may be utilized to facilitate insertion of the immunoadhesin into the adenoviral genome. General methods for these and other cloning procedures are set forth in Sambrook et al., "Molecular Cloning, a Laboratory Manual" Cold Spring Harbor Laboratory Press (1989). Once isolated, the immunoadhesin can also be modified for other purposes such as increased expression by altering specific codons, for example, or for increased binding to a receptor or a ligand.

Yet another example of a method of obtaining an immunoadhesin is to amplify the corresponding wild-type nucleic acid from the nucleic acids found within a host organism containing the wild-type nucleic acid and clone the amplified nucleic acid in an appropriate vector. One skilled in the art will appreciate that the amplification step may be combined with a mutation step, if desired, using primers not completely homologous to the target nucleic acid for example, to simultaneously amplify the nucleic acid and alter specific positions of the nucleic acid.

The nucleic acid encoding the immunoadhesin, however obtained, if not already in the context of an adenoviral genome, can be inserted into the selected adenoviral genome. Once the immunoadhesin is cloned into the adenoviral genome, or part of the adenoviral genome, this nucleic acid will generally be constructed such that the immunoadhesin is positioned adjacent to and under the control of an effective promoter. The promoter can be selected based upon the ultimate cell in which expression is desired. In certain cases, the promoter may comprise a prokaryotic promoter where the immunoadhesin is being adapted for expression in a prokaryotic host as well as in a eukaryotic vector. For example, the immunoadhesin may be expressed in a prokaryotic host under the direction of one promoter, while the same immunoadhesin may be expressed in a eukaryotic host under the direction of a eukaryotic promoter in the same construct. In other cases, the promoter may comprise only a eukaryotic promoter where the vector is being specifically adapted for expression in a eukaryotic host. Promoters of particular utility in the vectors of the invention comprise cytomegalovirus promoters and adenoviral promoters. Furthermore, an inducible promoter, such as a heat shock promoter, a metallothionein promoter, a lac-inducible promoter, a tetracycline-inducible promoter, or a repressible promoter can be used. Regardless of the exact nature of the immunoadhesin's promoters, the recombinant adenovirus of the present invention will incorporate a nucleic acid segment encoding an immunoadhesin as described herein.

The immunoadhesin inserted within the adenoviral genome can be positioned such that an adenovirus promoter is operatively linked to the immunoadhesin insert which adenoviral promoter can then direct transcription of the immunoadhesin nucleic acid, or the immunoadhesin insert may contain its own adenoviral promoter. Similarly, the immunoadhesin insert may be positioned wherein the nucleic acid encoding the immunoadhesin may utilize other adenoviral regulatory regions or sites such as splice junctions and polyadenylation signals and/or sites. Alternatively, the nucleic acid encoding an immunoadhesin may contain a different promoter or other regulatory sequences, such as splice sites and polyadenylation sequences, wherein the nucleic acid encoding the immunoadhesin may contain those sequences necessary for expression of the immunoadhesin and not partially or totally require these regulatory regions and/or sites of the adenovirus genome. These regulatory sites may also be derived from another source, such a virus other than adenovirus. For example, and as described herein, a polyadenylation signal from SV40 may be used rather than an adenovirus, a human, or a murine polyadenylation signal. The immunoadhesin nucleic acid insert may, alternatively, contain some sequences necessary for expression of the immunoadhesin and derive other sequences necessary for the expression of the immunoadhesin from the adenovirus genome, or even from the host in which the recombinant adenovirus is introduced.

As noted above, it is believed that, where desired, modification and changes may be made in the structure of the immunoadhesin and still obtain a molecule having like or otherwise desirable characteristics. Such changes may occur in natural isolates or may be synthetically introduced using site-specific mutagenesis, the procedures for which, such as mis-match PCR, are well known in the art.

For example, certain amino acids may be substituted for other amino acids in an immunoadhesin protein structure without appreciable loss of interactive binding capacity with structures such as antigen-binding regions of antibodies (or, e.g., binding sites on substrate molecules). Since it is the interactive capacity and nature of a protein that defines that protein's biological functional activity, certain amino acid sequence substitutions can be made in an immunoadhesin sequence (or, of course, its underlying nucleic acid sequence) and nevertheless obtain an immunoadhesin with like or even countervailing properties (e.g., antagonistic v. agonistic). It is thus contemplated by the inventors that various changes may be made in the sequence of the immunoadhesins (or underlying nucleic acid) without appreciable loss of their biological utility or activity and possibly with an increase in such utility or activity.

The present invention also provides an adenovirus comprising a recombinant nucleic acid encoding an immunoadhesin inserted within an adenoviral nucleic acid, wherein the recombinant nucleic acid can be packaged in an adenovirus particle and wherein expression of the nucleic acid encoding the immunoadhesin results in production of the immunoadhesin. Various adenoviruses may be used in the compounds and methods described herein. For example, and as described in the Example contained herein, a nucleic acid encoding an immunoadhesin can be inserted within the genome of adenovirus type 5. Similarly, other types of adenovirus may be used such as type 1, type 2, type 3, etc. For an exemplary list of the adenoviruses known to be able to infect human cells and which therefore can be used in the present invention, see Fields, et al. (1990) Virology, Raven Press, New York). Furthermore, it is contemplated that a recombinant nucleic acid comprising an adenoviral nucleic acid from one type adenovirus can be packaged using capsid proteins from a different type adenovirus.

The adenovirus is preferably rendered replication deficient, depending upon the specific application of the compounds and methods described herein. Methods of rendering an adenovirus replication deficient and are well known in the art. For example, mutations such as point mutations, deletions, and insertions, and combinations thereof, can be directed toward a specific adenoviral gene or genes, such as the E1 gene. For a specific example of the generation of a replication deficient adenovirus for use in gene therapy, see WO 94/28938 (Adenovirus Vectors for Gene Therapy Sponsorship) which is incorporated herein.

In one specific embodiment of the present invention, the recombinant nucleic acid encoding an immunoadhesin comprises a nucleic acid encoding an IL-10 functionally attached to a nucleic acid encoding an IgG polypeptide (IL-10-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. The term "functionally attached" as used herein is meant to describe IL-10, for example, is attached to IgG, for example, such that both molecules retain their respective specificities, and that the attachment of the two molecules to each other does not cause a decrease in their specificities or activities, but may increase one or both. In another embodiment of the present invention, the recombinant nucleic acid encoding an immunoadhesin comprises a nucleic acid encoding a vIL-10 functionally attached to a nucleic acid encoding an IgG polypeptide (vIL-10-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding an IL-13 functionally attached to a nucleic acid encoding an IgG polypeptide (IL-13-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding a LFA functionally attached to a nucleic acid encoding an IgG polypeptide (LFA-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding a mutated IL-2 functionally attached to a nucleic acid encoding an IgG polypeptide (IL-2ra-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding an IL-Ira (IL-1 receptor antagonist) functionally attached to a nucleic acid encoding an IgG polypeptide (IL-1ra-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. (Hannum et al. "Interleukin-1 Receptor Antagonist Activity of a Human Interleukin-1 Inhibitor" Nature 343:336–40 (1990) In yet another embodiment of the present invention, the recombinant nucleic acid encoding an immunoadhesin comprises a nucleic acid encoding a mutant IL-4 functionally attached to a nucleic acid encoding an IgG polypeptide (mutant IL-4-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding a VLA4 functionally attached to a nucleic acid encoding an IgG polypeptide (VLA4-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding an ICAM functionally attached to a nucleic acid encoding an IgG polypeptide (ICAM-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding a IL-2 functionally attached to a nucleic acid encoding an IgG polypeptide (IL-2-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding a TGF-β1 functionally attached to a nucleic acid encoding an TgG polypeptide (TGF-β1-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention the recombinant nucleic acid encoding an immunoadhesin comprises a nucleic acid encoding a TGF-β1$^{223,225}$ functionally attached to a nucleic acid encoding an IgG polypeptide (TGF-β1$^{23,225}$-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin. In yet another embodiment of the present invention, the recombinant nucleic acid encoding an immunoadhesin comprises a nucleic acid encoding a VCAM functionally attached to a nucleic acid encoding an IgG polypeptide (VCAM-IgG) inserted within an adenoviral nucleic acid, wherein the recombinant nucleic acid can be packaged in an adenovirus particle and wherein expression of the recombinant nucleic acid encoding the immunoadhesin results in production of the immunoadhesin.

In one embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises IL-10-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises vIL-10-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises IL-13-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises LFA-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises IL-2ra-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises IL-1ra-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises mutant IL-4-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises VLA4-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises ICAM-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises IL-2-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises TGF-β1-IgG. In another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises TGF-β1$^{223,}$ $_{225}$IgG. In yet another embodiment, the present invention provides an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin and wherein the immunoadhesin comprises VCAM-IgG.

Also provided by the present invention are other immunoadhesins wherein the immunoadhesins comprise the non-immunoglobulin molecules described herein and those known in the art, operatively linked to immunoglobulin molecules or fragments of immunoglobulin molecules such as the HFc domains, wherein the species of immunoglobulin is other than IgG1. Examples other subtypes of immunoglobulins which may be used include, but are not limited to, IgG2, IgM, IgE, and IgA.

Also provided by the present invention are compounds comprising nucleic acids encoding vIL-10-IgG, IL-13-IgG, LFA-IgG, IL-2ra-IgG, IL-1ra-IgG, mutant IL-4-IgG, VLA4-IgG, IL2-IgG, TGF-β1-IgG, TGF-β1$^{223,225}$-IgG, and VCAM-IgG.

Also provided by the present invention are compounds comprising proteins comprising vIL-10-IgG, IL-13-IgG, LFA-IgG, IL-2ra-IgG, IL-1ra-IgG, mutant IL-4-IgG, VLA4-IgG, IL2-IgG, TGF-β1-IgG, TGF-β1$^{223,225}$-IgG, and VCAM-IgG.

In all the constructions or compounds described herein, the non-immunoglobulin molecule may be functionally attached to a specifically cleavable linker peptide which is in turn functionally attached to an IgG polypeptide, such as by a thrombin-sensitive linker peptide. A linker such as this may allow one to specifically separate the non-immunoglobulin molecule from the immunoglobulin molecule in specific cells or tissues, or at specific times post administration. A functional attachment is typically, but not limited to, a peptide bond. Other additional sequences may also be attached to the immunoadhesin, either through the addition of a nucleic acid encoding the additional sequence, or by addition of a peptide to the immunoadhesin. Similarly, the specific immunoadhesins of the present invention may be obtained not only through expression of a nucleic acid, but through the synthesis of a polypeptide as well.

One method of producing proteins comprising the immunoadhesins of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert -butyloxycarbonoyl) chemistry. (Applied Biosystems, Inc., Foster City, Calif.). One skilled in the art can readily appreciate that a peptide or polypeptide corresponding to vIL-10, for example, can be synthesized by standard chemical reactions. For example, a peptide or polypeptide can be synthesized and not cleaved from its synthesis resin whereas the other fragment of an immunoadhesin can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an immunoadhesin. (Grant, G. A., "Synthetic Peptides: A User Guide" W. H. Freeman and Co., N.Y. (1992) and Bodansky, M. and Trost, B., Ed., "Principles of Peptide Synthesis" Springer-Verlag Inc., N.Y. (1993)). Alternatively, the peptide or polypeptide can by independently synthesized in vivo as described above. Once isolated, these independent peptides or polypeptides may be linked to form an immunoadhesin via similar peptide condensation reactions.

For example, enzymatic ligation of cloned or synthetic peptide segments can allow relatively short peptide fragments to be joined to produce larger peptide fragments, polypeptides or whole protein domains (Abrahmsen, L., et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson, et al., "Synthesis of Proteins by Native Chemical Ligation" Science, 266:776–779 (1994)). The first step is the chemoselective reaction of an unprotected synthetic peptide-%-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis, L, et al., FEBS Lett., 307:97 (1987), Clark-Lewis, I., et al., J. Biol. Chem., 269:16075 (1994), Clark-Lewis, I., et al., Biochemistry, 30:3128 (1991), and Rajarathnam, K., et al., Biochemistry, 29:1689 (1994)).

Alternatively, unprotected peptide segments can be chemically linked where the bond formed between the peptide segments as a result of the chemical ligation is an unnatural (non-peptide) bond (Schnolzer, M., et al., Science, 256:221 (1992)). This technique has been used to synthesize analogs of protein domains as well as large amounts of relatively pure proteins with full biological activity (deLisle Milton, R. C., et al., "Techniques in Protein Chemistry IV" Academic Press, New York, pp. 257–267 (1992)).

The invention also provides fragments of immunoadhesins which have bioactivity. The polypeptide fragments of the present invention can be recombinant proteins obtained by cloning nucleic acids encoding the polypeptide in an expression system capable of producing the polypeptide fragments thereof, such as the adenovirus system described herein. For example, one can determine the active domain of vIL-10 which can cause a biological effect associated with the vIL-10. In one example, amino acids found to not contribute to either the activity or the binding specificity or affinity of the vIL-10 can be deleted without a loss in the respective activity.

For example, amino or carboxy-terminal amino acids can be sequentially removed from either the native or the modified non-immunoglobulin molecule or the immunoglobulin molecule and the respective activity assayed in one of many available assays. In another example, a fragment of an immunoadhesin can comprise a modified vIL-10 wherein at least one amino acid has been substituted for the naturally occurring amino acid at a specific position, and a portion of either amino terminal or carboxy terminal amino acids, or even an internal region of the vIL-10, has been replaced with a polypeptide fragment or other moiety, such as biotin, which can facilitate in the purification of the modified immunoadhesin. For example, a modified immunoadhesin can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified immunoadhesin receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

Active fragments of an immunoadhesin can also be synthesized directly or obtained by chemical or mechanical disruption of a larger immunoadhesin. An active fragment is defined as an amino acid sequence of at least about 5 consecutive amino acids derived from the naturally occurring amino acid sequence, which has the relevant activity, e.g., binding or regulatory activity.

The fragments, whether attached to other sequences or not, can also include insertions, deletions, substitutions, or other selected modifications of particular regions or specific amino acids residues, provided the activity of the peptide is not significantly altered or impaired compared to the non-modified immunoadhesin or immunoadhesin fragment. These modifications can provide for some additional property, such as to remove/add amino acids capable of disulfide bonding, to increase its bio-longevity, to alter its secretory characteristics, etc. In any case, the peptide must possess a bioactive property, such as binding activity, regulation of binding at the binding domain, etc. Functional or active regions of the immunoadhesin may be identified by mutagenesis of a specific region of the protein, followed by expression and testing of the expressed polypeptide. Such methods are readily apparent to a skilled practitioner in the art and can include site-specific mutagenesis of the nucleic acid encoding the receptor. (Zoller, M. J. et al.).

The present invention also provides a method of delivering an immunoadhesin to a cell comprising administering to the cell an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin, whereby expression of the recombinant nucleic acid produces the immunoadhesin, thereby delivering the immunoadhesin to the cell. Such administration can result in highly successful delivery of the nucleic acid to cells and thus relatively high levels of expression of the immunoadhesin.

It is well known in the art that an adenovirus can infect a wide variety of cells and therefore deliver its nucleic acid to the host cell, which in turn, can then express the nucleic acid, thereby producing the proteins encoded by the adenoviral nucleic acid. For example, adenovirus can infect various sites of the respiratory tract, the eye, muscle cells, cells of the gastrointestinal tract, and cells of the bladder. The cell to which the adenovirus comprising a nucleic acid encoding an immunoadhesin is administered may comprise a cell ex vivo, such as a cell removed from a subject which is administered the adenovirus and subsequently replaced back to the subject. Alternatively, the cell may comprise a cell in vivo, such as delivering the adenovirus comprising the recombinant nucleic acid encoding an immunoadhesin to a cell within or on a subject. Alternatively, the cell may comprise a cell in culture, such as delivering to tissue culture cells an adenovirus comprising an immunoadhesin.

This method, therefore, can be used to deliver an immunoadhesin to a particular cell or a group of cells, or alternatively, to a particular tissue or organ. Once an adenovirus comprising an immunoadhesin or a recombinant nucleic acid encoding an immunoadhesin is administered to a cell, that cell can then express the recombinant nucleic acid encoding the immunoadhesin and thereby produce the immunoadhesin, which can have a biological response from that cell or other cells which contact the immunoadhesin or are otherwise affected by the immunoadhesin.

The fact that adenovirus infects the eye is particularly relevant to a specific embodiment of the present invention which provides a method of delivering an immunoadhesin to a human retinal pigment epithelial cell comprising administering to the human retinal pigment epithelial cell an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin, whereby expression of the recombinant nucleic acid produces the immunoadhesin, thereby delivering the immunoadhesin to the human retinal pigment epithelial cell.

Similarly, adenovirus can infect muscle cells, including skeletal myocyte muscle cells. One can therefore deliver an adenovirus comprising a recombinant nucleic acid encoding an immunoadhesin to these cells to deliver the immunoadhesin to these cells to treat a variety of conditions.

Similarly, the present invention also provides a method of producing an immunoadhesin comprising administering to a cell an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin, whereby the cell expresses the recombinant nucleic acid encoding the immunoadhesin, thereby producing the immunoadhesin. This method can therefore be used to produce immunoadhesins which are secreted extracellularly in which the immunoadhesin can be harvested from the extracellular medium as well as those immunoadhesins which are not secreted from the cell, in which the cell may have to be disrupted, possibly including additional disruption of the cell membrane. In a preferred embodiment, the immunoadhesins are secreted readily from the cells. Protein harvesting methods are standard in the art and exemplified herein. The immunoadhesin can be purified to any desired level of purity, as is also standard in the art.

Additionally, and as described herein, the cell which is administered the nucleic acid encoding an immunoadhesin or an adenovirus comprising a nucleic acid encoding an immunoadhesin may produce the immunoadhesin, a subsequent adenovirus comprising a nucleic acid encoding an immunoadhesin, or both. The present invention therefore provides a method of producing an adenovirus comprising a nucleic acid encoding an immunoadhesin.

Similarly, the present invention also provides a method of delivering an immunoadhesin to a subject comprising administering to the subject an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin, whereby a cell of the subject expresses the recombinant nucleic acid encoding the immunoadhesin, thereby delivering the immunoadhesin to the subject.

Also provided by the present invention is a method of treating an inflammatory condition in a subject comprising administering to the subject an adenovirus comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin protein, whereby a cell in the subject expresses the recombinant nucleic acid encoding the immunoadhesin and produces the immunoadhesin, thereby treating the inflammatory condition.

In one embodiment and as described in the Example contained herein, the immunoadhesin encoded by the adenovirus nucleic acid comprises IL-10-IgG. In another embodiment, the inflammatory condition comprises uveitis.

Also provided by the present invention is a method of treating an inflammatory condition in a subject comprising administering to the subject a compound comprising a recombinant nucleic acid encoding an immunoadhesin inserted within an adenoviral nucleic acid, wherein the recombinant nucleic acid can be packaged in an adenovirus particle and wherein expression of the recombinant nucleic acid encoding the immunoadhesin results in production of the immunoadhesin, whereby the subject expresses the recombinant nucleic acid encoding the immunoadhesin and produces the immunoadhesin, thereby treating the inflammatory condition. The recombinant nucleic acid encoding the immunoadhesin may be replication competent or replication deficient, but is preferably replication deficient. This method therefore provides a method for treating an inflammatory condition in a subject by administering a recombinant nucleic acid -encoding an immunoadhesin to the subject whereby the subject expresses the recombinant nucleic acid encoding the immunoadhesin thereby producing the immunoadhesin which treats the inflammatory condition. Methods of administering the recombinant nucleic acid encoding the immunoadhesin are well known in the art and can include administration of "naked DNA" as well as a nucleic acid associated with a carrier such as a cationic or anionic liposome, or polylysine. (See, e.g. Brigham et al. Amer. J. Respir. Cell and Mol. Biol. 8:209–213 (1993); Felgner et al. Proc. Nat. Acad. Sci. USA 84:7413; and U.S. Pat. No. 4,897,355 (Eppstein et al.)).

An immunoadhesin or a nucleic acid encoding an immunoadhesin used in these methods of treating an inflammatory condition in a subject comprising administering to the subject an immunoadhesin or a recombinant nucleic acid encoding an immunoadhesin are selected from the group consisting of vIL-10-IgG, IL-13-IgG, LFA-IgG, IL-2ra-IgG, IL-1ra-IgG, mutant IL-4-IgG, VLA4-IgG, Il-2-IgG, TGF-β1-IgG, TGF-β1$^{223,225}$-IgG, and VCAM-IgG. Where the subject is administered a nucleic acid encoding an immunoadhesin, that subject expresses the nucleic acid encoding the immunoadhesin, thereby providing the subject with the immunoadhesin. Expression of the nucleic acid encoding the immunoadhesin typically occurs within cells of the subject.

A compound comprising an adenovirus comprising a nucleic acid encoding an immunoadhesin, a recombinant nucleic acid encoding an immunoadhesin, or an immunoadhesin of this invention can be administered to a subject in need thereof by commonly employed methods for administering compounds in such a way to bring the adenovirus and/or the immunoadhesin in contact with the tissue or cell to be treated. Such methods include oral administration, parenteral injection (IP), subcutaneous injection (SC—particularly a controlled release depot), intravenous injection (IV), intramuscularly (IM), intranasal (IN), intraocular (IO), extraocular (EO), sublingual (SL), or orally such as through oral inhalation (OI). In general, a therapeutically effective amount is that amount needed to achieve the desired results, thus successfully treating of the targeted disease state. Articles by George Hiller, *Advanced Drug-Delivery Reviews*, 10: 163–204 (1993) [Elsevier Science Publishers B. V.] and Lorraine L. Wearley, *Critical Reviews in Therapeutic Drug Carrier Systems*, 8(4): 331–394 (1991) are useful discussions of these types of administrations. These articles are incorporated herein by reference.

The dosage ranges for the administration of a compound or compositions of this invention may depend upon its potency, as described further herein, and are amounts large enough to produce the desired effect in which the condition being treated is treated, e.g. is measurably prevented, inhibited or decreased. The dosage should not be so large as to cause adverse side effects. Generally, the dosage will vary with the age, condition, sex and extent of the condition in the subject and can be determined by one of skill in the art. The dosage can also be adjusted by the individual physician in the event of any complication. The dosage can be that amount typical for related adenovirus administrations, such as about $1\times10^2$ to about $1\times10^{12}$ plaque-forming units of adenovirus and can be, for example, $1\times10^2$ pfu, $1\times10^3$ pfu, $1\times10^4$ pfu, $1\times10^5$ pfu, $1\times10^6$ pfu, $1\times10^7$ pfu, $1\times10^8$ pfu, $1\times10^9$ pfu, $1\times10^{10}$ pfu, $1\times10^{11}$ pfu, $1\times10^{12}$ pfu. For administration of recombinant immunoadhesin, the dose can range from about 0.001 to about 10 mg/kg and can be, for example, about 0.01 to about 10 mg/kg; about 0.1 to about 10 mg/k; about 1.0 to about 10 mg/kg; about 0.001 to about 1 mg/kg; about 0.001 to about 0.1 mg/kg; and about 0.01 to about 1.0 mg/kg. For one trial the dose used was up to 1 mg/kg (See, Hodges et al. "Phase 1 Study of Recombinant Human CD4-Immunoglobulin G Therapy of Patients with AIDS and AIDS-related Complex" Antimicrob. Agents Chemother. 35:2580–6 (1991).

The therapeutic compounds or compositions of this invention are conventionally administered, whether by IP, IM, IV, IN, IO, EO, SubCu, etc., as of a unit dose. The term "unit dose" when used in reference to a therapeutic compound or composition of the present invention refers to physically discrete units suitable as unitary dosage for the subject, each unit containing a predetermined quantity of active material calculated to produce the desired therapeutic effect in association with the required diluent; i.e., carrier, or vehicle.

The compounds or compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application may depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Another aspect of this invention is a pharmaceutically-acceptable therapeutic composition that comprises a therapeutically effective amount of an adenovirus or an immunoadhesin of this invention in combination with a pharmaceutically-acceptable excipient. The composition is designed to facilitate the method of administering an adenovirus or an immunoadhesin of this invention in an effective manner. Generally a composition of this invention will have an adenovirus or an immunoadhesin dissolved or dispersed in the pharmaceutically-acceptable excipient.

As used herein, the terms "pharmaceutically acceptable", "physiologically tolerable" and grammatical variations thereof, as they refer to compositions, excipients (including carriers, diluents, stabilizers, lubricants, reagents and the like), are used interchangeably and represent that the materials are capable of administration to or upon a subject without toxicity and preferably without the production of undesirable physiological effects such as nausea, dizziness, gastric upset and the like.

Compounds or compositions of this invention may be administered to a subject in a variety of forms depending on the method of administration. The method of administration may be viewed as "invasive" (e.g., IV, IM, IP or SC) or "non-invasive" (e.g., ocular, buccal, oral, transdermal, rectal, NI, OI [pulmonary], and the like). In general, a composition that is delivered by an invasive route is generally administered by a health care professional while a composition delivered by a non-invasive route may be administered by the patient him-or herself.

In administering the compounds or compositions of the invention by non-invasive method there are various general methods that are used for enhancing the delivery of a compound comprising an adenovirus containing a nucleic acid encoding an immunoadhesin, a nucleic acid encoding an adenovirus encoding an immunoadhesin, or an immunoadhesin. The first is to increase the absorption of the compound. This can be done by the use of a prodrug, chemical modification of the primary structure of the compound, incorporation of the compound into liposomes or other encapsulation material, co-administration with penetration enhancers, the use of physical methods such as iontophoresis and phonophoresis and targeting to specific tissues. Another method for enhancing delivery is to minimize the metabolism of the compound. This would include chemical modification of the primary structure, covalent attachment to a polymer, incorporation into a liposome or other encapsulation material, co-administration with an enzyme inhibitor and targeting to specific tissues. The third general method of enhancing delivery of the compound includes prolonging the half-life of the compound by protecting it with polymers or liposomes, using a bioadhesive material or targeting the composition to a specific tissue.

In general, if it is desired to increase the absorption of the compounds of this invention through ocular, buccal, transdermal, or rectal administration, or by nasal inhalation or oral inhalation, one can employ certain penetration enhancers. These enhancers can include chelators such as EDTA, citric acid, N-acyl derivatives of collagen, enamines (N-Amino N-acyl derivatives of β-diketones). Surfactants can also be used to enhance penetration. These include, sodium lauryl sulfate, polyoxyethylene-9-lauryl ether and polyoxyethelene-20-cetyl ether. Bile salts and derivatives are also known to enhance the penetration of the compound and these include sodium deoxycholate, sodium glycocholate, sodium taurocholate, sodium taurodihydrofusidate and sodium glycodihyrofusidate. Still another type of penetration enhancer useful in the composition of this invention includes ceratin fatty acids and derivatives such as oliec, caprylic acid, capric acid, acylcarnitines, acylcholine and mono and diglycerides. Nonsurfactants are also useful as penetration enhancers. The penetration enhancers can be used in the solution with the compounds of this invention where the compound and the penetration enhancers are in a pharmaceutically acceptable sterile solution which can be administered, for example by ocular administration. Alternatively the penetration enhancers can be included in a powdered formulation that can be administered as a aerosol by suspending the particulate matter in the stream of air. Such powdered formulations can be administered by a dry-powder inhaler such as those represented by Ventolin Rotohaler (Glaxo, Inc., Research Triangle Park, N.C., U.S.A), and Spinhaler (Fisons Corporation, Bedford, Me.). Compositions that are in the form of solid micronized particle having a particle size of about 0.5 to 10 microns in median diameter may be prepared in accordance with the teaching of PCT application international publication numbers WO91/16038 and WO93/00951. Powders may be prepared in accordance with the teaching of Remington's Pharmaceutical Sciences, 18th Edition, Mack Publishing Co., Chapter 88: 1645–1648. These teachings are incorporated herein by reference.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. In preparing oral formulations one needs to be aware of the problems of degradation in the mouth and upper GI tract. Thus, it may be preferable to employ an enzyme inhibitor in combination with the compound, or to use a penetration enhancer or to use a protective polymer or microcapsule. The percentage of the compositions and preparations may, of course, be varied and may conveniently contain up to about 20% by weight of the compound in a dosage unit. The amount of active compound in such therapeutically useful compositions is such that a suitable dosage will be obtained.

The tablets, troches, pills, capsules and the like may also contain excipients such as the following: a binder such as polyvinylpyrrolidone, gum tragacanth, acacia, sucrose, corn starch, gelatin, calcium phosphate, sodium citrate, and calcium carbonate; a disintegrant such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed. In addition, the active compound may be incorporated into sustained-release preparations and formulations. Further components may be apparent to one of ordinary skill in the art.

For purposes of IP administration, solutions in sesame or peanut oil or in aqueous propylene glycol can be employed, as well as sterile aqueous solutions of the corresponding water-soluble, alkali metal or alkaline-earth metal salts. Such aqueous solutions should be suitably buffered and the liquid diluent first rendered isotonic with sufficient saline or glucose. Solutions of the active compound as a free base or a pharmacologically acceptable salt can be prepared in water suitably mixed with e.g. hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for IV, IM, SC and IP. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, and as required and appropriate, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For IP formulations that are controlled-release, a compound of this invention can be combined with a polymer that regulates the release of the compound and protects it from degradation. Generally such polymer may be biodegradable or non-biodegradable and may further be hydrophilic or hydrophobic. Suitable hydrophilic, non-degradable polymers for use in the composition of this invention include hydrogels such as acrylamide or vinyl pyrrolidone crosslinked with N, N'-methylene bisacrylamide. Suitable non-degradable hydrophobic polymers include, ethylene/vinyl acetate copolymers, silicone elastomers, polydimethylsiloxane, and the like. Degradable hydrophilic polymers useful in this invention include N-vinyl pyrrolidone or acrylamide crosslinked with less than 1% N, N'-methylene bisacrylamide, dextran derivatized with glycidyl methacrylate and crosslinked with N, N'-methylene bisacrylamide, water-soluble polyester prepared from fumaric acid and poly (ethylene glycol) and crosslinked with N-vinyl pyrrolidone, water-soluble polyesters, and the like. Suitable degradable hydrophobic polymers useful for the composition of this invention include lactide/glycolide co-polymers, poly (orthoesters) and polyanhydrides. Of these various polymers, the lactide/glycolide co-polymers are preferred. A more detailed description of these polymers for controlled parenteral delivery may be found in an article by George Heller, *Advanced Drug-Delivery Reviews,* 10:163–204 (1993) (Elsevier Science Publishers BV). The article is incorporated herein by reference.

For the preferred controlled release composition of this invention the lactide/glycolide co-polymers may have a ratio of DL-a lactic acid to DL-glycolic acid of about 30:70 to about 70:30, preferably about 40:60 to about 60:40. A ratio of about 44:56 is representative. An adenovirus or immunoadhesin of this invention can be microencapsulated in the copolymer by means known in the art to form the composition, see, for example, U.S. Pat. No. 4,675,189 issued Jun. 23, 1987 to Sanders, Kent, Lewis and Tice.

For purposes of topical administration, dilute sterile, aqueous solutions (usually in about 0.1% to 5% concentration), otherwise similar to the above parenteral solutions, are prepared in containers suitable for drop-wise administration to the eye in appropriate vehicles such as saline with appropriate antimicrobial agents such as sodium benzoate and thimerasol.

The dosage of the present therapeutic agents which will be most suitable for prophylaxis or treatment will vary with the form of administration, the particular compound chosen and the physiological characteristics of the particular subject under treatment. Generally, small dosages may be used initially and, if necessary, increased by small increments until the optimum effect under the circumstances is reached. Oral administration may require higher dosages.

Also provided by the present invention is a method of screening an immunoadhesin for bioactivity, comprising administering to a first cell an adenovirus containing a recombinant nucleic acid encoding the immunoadhesin, wherein the first cell expresses the recombinant nucleic acid encoding the immunoadhesin and thereby produces the immunoadhesin, contacting a second cell with the immunoadhesin, and monitoring the second cell for a biological response to the immunoadhesin, thereby screening the immunoadhesin for bioactivity. This method can therefore screen particular immunoadhesins for a particular bioactivity such as reduction of cell-mediated immunity, reduction of antibody-mediated immunity, reduction of tissue necrosis and apoptosis and reduction of extracellular fluid extravasation.

The screening method may entail harvesting the immunoadhesin from the first cell which produces the immunoadhesin before the immunoadhesin is administered to a second cell which is then monitored for a biological response to the immunoadhesin, or the method may entail admixing the first cell which produces the immunoadhesin with the second cell which is then monitored for a biological response to the immunoadhesin. Similarly, the first cell which produces the immunoadhesin may be the same cell type as the second cell or the first and second cells may be different cell types.

The present invention also provides a method of screening an immunoadhesin for bioactivity comprising administering to a cell an adenovirus containing a recombinant nucleic acid encoding the immunoadhesin, wherein the cell expresses the recombinant nucleic acid encoding the immunoadhesin and thereby produces the immunoadhesin, and monitoring the cell for a biological response to the immunoadhesin, thereby screening the immunoadhesin for bioactivity. The screening method, therefore, does not require a second cell which may not be producing an immunoadhesin, but may be employed using only a cell which is itself producing an immunoadhesin.

The screening assays of the invention may conveniently employ the immunoadhesin directly from the cell in which it is produced. This is achieved most preferably by simply expressing the selected immunoadhesin within the cell, typically a eukaryotic cell, followed by preparing a sample of the cell culture medium which includes the immunoadhesin. A portion of the culture medium may then be admixed with an appropriate effector of the immunoadhesin, e.g., a specific interleukin receptor. Alternatively, an additional purification step is accomplished on the culture medium containing the immunoadhesin in order to recover a purified quantity of immunoadhesin molecules. The additional purification steps may include specific binding of the immunoadhesin to protein A, anti-mouse IgG or, using affinity chromatography with a lectin column such as concanavalin A or lentil lectin.

By comparing the binding of the selected effector in the presence or absence of the candidate immunoadhesin, one can obtain information regarding the binding properties of the immunoadhesin. There are believed to be a wide variety of embodiments which can be employed to determine the effect of the immunoadhesin on cells, and the invention is not intended to be limited to any one such method. However, it will generally be desirable to employ a system wherein one can measure the ability of the immunoadhesin to bind to and or be modified by the effector employed to a particular receptor. One method which may be employed may use a labeled immunoadhesin, which has been labeled in a manner such that the label is quantitatively retained in the resultant immunoadhesin/receptor complex. A convenient approach is the use of a radioactive label, such as $^{125}I$, $^{14}C$ or $^{3}H$, which may be directly quantitated in both the immunoadhesin and the resultant complex. In certain assays, the admixture containing the immunoadhesin and a receptor is allowed to incubate for a selected amount of time, and the resultant incubated mixture subjected to a separation means in order to separate the unbound immunoadhesin remaining in the admixture from any immunoadhesin/receptor complex so produced. Then, one simply measures the amount of each, e.g., versus a control to which no candidate immunoadhesin has been added. This measurement can be made at various time points where velocity data is desired. From this, one may determine the ability of the immunoadhesin to alter or modify the function of the receptor. Numerous techniques are known which could be employed for the separation of the immunoadhesin from immunoadhesin/receptor complex, and all such methods are intended to fall within the scope of the invention. Use of thin layer chromatographic methods (TLC), HPLC, spectrophotometric, gas chromatographic/mass spectrophotometric or NMR analyses. Other, more specific methods of purification already noted (affinity binding or immunoprecipitation) may be used, as well. It is contemplated that any such technique may be employed so long as it is capable of differentiating between the immunoadhesin and complex, and can be used to determine enzymatic function such as by identifying or quantifying the substrate and product. The immunoadhesin/receptor complex itself may also be the subject of techniques such as x-ray crystallography.

The screening methods described herein can also be utilized to screen an immunoadhesin for bioactivity, comprising administering to a first cell an adenoviral nucleic acid encoding the immunoadhesin, wherein the first cell expresses the adenoviral nucleic acid encoding the immunoadhesin and thereby produces the immunoadhesin, contacting a second cell with the immunoadhesin, and monitoring the second cell for a biological response to the immunoadhesin, thereby screening the immunoadhesin for bioactivity.

Similarly, the screening methods described herein can be utilized to screen an immunoadhesin for bioactivity comprising administering to a cell an adenoviral nucleic acid encoding the immunoadhesin, wherein the cell expresses the adenoviral nucleic acid encoding the immunoadhesin and thereby produces the immunoadhesin, and monitoring the cell for a biological response to the immunoadhesin, thereby screening the immunoadhesin for bioactivity.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the accompanying claims.

The following examples are set forth so as to provide those of ordinary skill in the art with a complete disclosure and description of how the methods claimed herein may be performed, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLES

Cells

Human retinal pigment epithelial cell (hRPE) primary cultures were established from bank eyes (provided generously by the Missouri Lion's Eye Tissue Bank, Columbia, Mo.). The anterior segment, vitreous body, and retina were dissected away from the posterior segment. The choroid and retinal pigment epithelium (RPE) were then teased away from the sclera and incubated in Eagle's minimal essential medium (EMEM; Gibco-BRL, Gaithersburg, Md.) containing 0.1 mg/ml Dispase (Boehringer Mannheim, Indianapolis, Ind.) for 16 hours at 37° C. in a 5% $CO_2$ humidified air incubator. The cells were then removed by gentle pipetting and shaking followed by centrifugation at 33×g for 5 minutes. Cells were then resuspended in RPE growth medium (EMEM supplemented with non-essential amino acids (Gibco-BRL), penicillin G (Gibco-BRL) at 140 U/ml, streptomycin (Gibco-BRL) at 140 µg/ml, amphotericin B (Gibco-BRL) at 0.35 ng/ml, and fetal bovine serum (Gibco-BRL) at 10%. Cells were then transferred to a tissue culture dish and maintained as a monolayer in a 5% $CO_2$ humidified air incubator at 37° C. The retinal pigment epithelial origin of cultures was confirmed by the presence of staining for keratin and PHM-5 (Silenius). All experiments were carried out on cells between passage ten and seventeen.

The transformed human kidney cell line 293 (American Type Culture Collection, Rockville, Md.) was maintained as a monolayer in Improved Eagle's Minimum Essential Medium (IMEM, Biofluids), supplemented with L-glutamine at 10 mM (Gibco-BRL), penicillin G at 50 units/ml, streptomycin at 50 µg/ml, and 10% heat-inactivated fetal bovine serum (Hyclone) in a 5% $CO_2$ humidified air incubator at 37° C. Transfections and transductions were performed generally at 60–80% confluence.

NIH/3T3 (gift of S. Aaronson, National Cancer Institute/National Institutes of Health) and C9, (a Chinese hamster ovary cell line derived from CHO-K1; gift of D. Valle, Johns Hopkins University) cell lines were maintained in culture in Dulbecco's Modified Essential Medium (DMEM, Biofluids) and 10% heat-inactivated fetal bovine serum (Biofluids) in a 5% $CO_2$ humidified air incubator at 37° C.

ARPE-19, a spontaneously arising human RPE cell line (Dunn et al., 1996) (kindly provided by L. M. Hjelmeland) were maintained in culture medium consisting of Dulbecco's Modified Essential Medium: Nutrient Mixture F12, 1:1 mixture, with HEPES buffer (Biowhittaker), 10% fetal bovine serum (Hyclone), and 0.348% (w/v) additional sodium bicarbonate (56 mM final bicarbonate concentration) in a 10% $CO_2$ humidified air incubator at 37° C.

The IL-3 dependent pro-B cell line BaMR29a1 (generous gift of Dr. Kevin W. Moore, DNAX, Palo Alto, Calif.), transfected with the gene for the murine IL-10 receptor (mIL-10r) and neomycin resistance gene (Ho et al., 1993) maintained in culture in RPMI 1640 (Biowhittaker) with 50 µM mercaptoethanol (Sigma), 10 ng/ml mouse IL-3 (R&D Systems), 1 mg/ml G418 (Gibco-BRL), and 10% fetal bovine serum (Gibco-BRL) in a 5% CO2 humidified air incubator at 37° C.

Construction of mIL-10:HFc/Ad5.hCMV.mIL-10:HFc

An immunoadhesin comprising murine interleukin-10 and the constant region of the murine IgGI heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV. 1. The shuttle plasmid pAd.CMV.mIL-10.HFc was generated by cloning the 534 bp PCR product encoding murine IL-10 (mIL-10) (Moore et al., 1990), lacking its termination codon and engineered with Eco RV and Xba I at its 5' and 3' ends respectively using primer sequences mIL-10 forward 5'-TGTATGATATCATGCCTGGCTCAGCACTG (SEQ ID NO:10) and mIL-10 reverse 5'-TGTATTCTAGAGCTTTTCATTTTGATCATCAT (SEQ ID NO:11), into the pAd.CMV.HFc construct in frame with HFc. In order to rescue a recombinant adenovirus, 10 µg of pAd.CMV.mIL-10.HFc was cotransfected by calcium phosphate coprecipitation (Wigler et al., 1977) into 293 cells along with 5 µg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid was exceeded by approximately 2 kb (McGrory et al., 1988).

Homologous recombination then took place in the 293 cells between the two plasmids replacing the E1 region and pBRX in JM17 with the cDNA from pAd.CMV.mIL-10:HFc. The resulting DNA was then be packaged into the adenovirus capsid and was also rendered replication-defective as a consequence of its lacking of the E1 region required for efficient replication. E1 was supplied in trans by the 293 cells. Single plaques of Ad5.hCMV.mIL-10:HFc were amplified in 293 cells from which crude viral lysate (CVL) was used for cell line transduction and the generation of serum-free conditioned medium. CVL was titered as described previously (Graham and Prevec, 1991) and was typically in the range of 7–9×10⁸ plaque forming units per milliliter (pfu/ml). Stocks of CVL generated from recombinant viruses were examined for contamination with replication competent adenovirus by infecting A549 cells (an epithelial cell line derived from human lung) at a multiplicity of infection (MOI) of 10 and serially passaged three times without observed cytopathic effect.

Construction of other immunoadhesins

For the purpose of screening the activity of these proteins in a rodent model of uveitis, the constructs listed were all murine or rat derived. It is important to note that the human derived constructs (both of the ligand and the IgG portion) are readily generated for use in treatment of human disease, using human interleukins and human immunoglobulins, which are known in the art.

vIL-10-IgG:

An immunoadhesin comprising viral interleukin-10 and the constant region of the murine IgG1 heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC 18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV.1. The shuttle plasmid pAd.CMV.vIL-10.HFc was generated by cloning the 510 bp PCR product encoding viral IL-10 (vIL-10) (Moore et al., 1990), lacking its termination codon and engineered with Eco RV and Xba I at its 5' and 3' ends respectively using primer sequences vIL-10 forward 5'-TGTATGATATCATGGAGCGAAGGTTAGTG (SEQ ID NO:12) and vIL-10 reverse 5'-TGTATTCTAGACCTGGCTTTAATTGTCATG (SEQ ID NO:13), into the pAd.CMV.HFc construct in frame with HFc. In order to rescue a recombinant adenovirus, 10 µg of pAd.CMV.vIL-10.HFc was cotransfected by calcium phosphate coprecipitation (Wigler et al., 1977) into 293 cells along with 5 µg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units.

Homologous recombination then takes place in the 293 cells between the two plasmids replacing the E1 region and pBRX in JM17 with the cDNA from pAd.CMV.vIL-10:HFc. The resulting DNA can then be packaged into the adenovirus capsid and was also rendered replication-defective as a consequence of its lacking of the E1 region required for efficient replication. E1 was supplied in trans by the 293 cells. Single plaques of Ad5.hCMV.vIL-10:HFc were amplified in 293 cells from which crude viral lysate (CVL) was used for cell line transduction and the generation of serum-free conditioned medium.

IL-13-IgG:

An immunoadhesin comprising interleukin-13 and the constant region of the murine IgG1 heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV.1. The shuttle plasmid pAd.CMV.IL-13.HFc was generated by cloning the 391 bp PCR product encoding IL-13. (Brown et al. (1989) "A family of small inducible proteins secreted by leukocytes are members of a new superfamily that includes leukocyte and fibroblast-derived inflammatory agents, growth factors, and indicators of various activation processes" J Immunology 142, 679–687), lacking its termination codon and engineered with Eco RV and Xba I at its 5' and 3' ends respectively using primer sequences IL-13 forward 5' TGTAT GATATCATG GCGCTCTG GGTGACT (SEQ ID NO:14) and IL-13 reverse 5'-TGTATTCTAGAGAAGGGGCCGTGGCGAA (SEQ ID NO:15), into the pAd.CMV.HFc construct in frame with HFc. In order to rescue a recombinant adenovirus, 10 µg of pAd.CMV.IL-13.HFc was cotransfected by calcium phosphate coprecipitation (Wigler et al., 1977) into 293 cells along with 5 µg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units.

Homologous recombination then takes place in the 293 cells between the two plasmids replacing the E1 region and pBRX in JM17 with the cDNA from pAd.CMV.IL-13:HFc. The resulting DNA was then packaged into the adenovirus capsid and was also rendered replication-defective as a consequence of its lacking of the E1 region required for efficient replication. E1 is supplied in trans by the 293 cells. Single plaques of Ad5.hCMV.IL-13:HFc were amplified in 293 cells from which crude viral lysate (CVL) was used for cell line transduction and the generation of serum-free conditioned medium.

IL-2ra-IgG:

An immunoadhesin comprising mutant interleukin-2 (capable of binding the interleukin-2 receptor without subsequent activation) and the constant region of the murine IgGI heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC 18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV.1. The shuttle plasmid pAd.CMV.mutant IL-2.HFc was generated by cloning the PCR product encoding mutant -IL-2 (IL-2) (Zurawski, G. (1989) EMBO J 8, 2583–90), lacking its termination codon and engineered with Eco RV and Xba I at its 5' and 3' ends respectively using primer sequences mutant IL-2 forward 5'-TGTATGATATCATG TACAGCACT-GAGCTC (SEQ ID NO:16) and mutant IL2 reverse 5'-TGTATTCTAGA TTGAGGGCTTGTTGAGATG (SEQ ID NO:17), into the pAd.CMV.HFc construct in frame with HFc. In order to rescue a recombinant adenovirus, 10 µg of pAd.CMV.mutant IL-2.HFc was cotransfected by calcium phosphate coprecipitation (Wigler et al., 1977) into 293 cells along with 5 μg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid was exceeded by approximately 2 kb (McGrory et al., 1988).

Homologous recombination then takes place in the 293 cells between the two plasmids replacing the E1 region and pBRX in JM17 with the cDNA from pAd.CMV.mutant IL-2:HFc. The resulting DNA was then packaged into the adenovirus capsid and was also rendered replication-defective as a consequence of its lacking of the E1 region required for efficient replication. E1 was supplied in trans by the 293 cells. Single plaques of Ad5.hCMV.mutant IL-2:HFc are amplified in 293 cells from which crude viral lysate (CVL) was used for cell line transduction and the generation of serum-free conditioned medium.

IL-ira-IgG:

An immunoadhesin comprising interleukin-1 receptor antagonist (IL1ra) and the constant region of the murine IgG1 heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV. 1. The shuttle plasmid pAd.CMV.IL1ra.HFc was generated by cloning the 533 bp PCR product encoding IL-Ira (Matsushime, H., Roussel, M. F., Matsushima, K, Hishinuma, A, Sherr, C. J.., (1991) Cloning and expression of murine interleukin-1 receptor antagonist in macrophages stimulated by colony-stimulating factor 1. Blood 78, 616–23.), lacking its termination codon and engineered with Hind III and Xba I at its 5' and 3' ends respectively using primer sequences IL1ra forward 5'-TGTATAAGCTTATGGAGCGAAGGTTAGTG (SEQ ID NO:18) and IL1ra reverse 5'-TGTATTCTAGACCTGGCTTTAATTGTCATG (SEQ ID NO: 13), into the pAd.CMV.HFc construct in frame with HFc. In order to rescue a recombinant adenovirus, 10 μg of pAd.CMV.IL1ra.HFc was cotransfected by calcium phosphate coprecipitation (Wigler et al., 1977) into 293 cells along with 5 μg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid is exceeded by approximately 2 kb (McGrory et al., 1988).

Homologous recombination then takes place in the 293 cells between the two plasmids replacing the E1 region and pBRX in JM17 with the cDNA from pAd.CMV.IL1ra:HFc. The resulting DNA was then packaged into the adenovirus capsid and was also rendered replication-defective as a consequence of its lacking of the E1 region required for efficient replication. E1 is supplied in trans by the 293 cells. Single plaques of Ad5.hCMV.IL1ra:HFc were amplified in 293 cells from which crude viral lysate (CVL) was used for cell line transduction and the generation of serum-free conditioned medium.

mutant 4-IgG:

An immunoadhesin comprising mutant interleukin-4 (mutant IL-4) and the constant region of the murine IgG1 heavy chain is produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 is constructed as described previously (Sullivan et al., 1996). The plasmid pAd/CMV.1 is then modified to contain the murine immunoglobulin gamma 1 heavy chain gene hinge, CH2, and CH3 domains (HFc). To engineer this construct, the HFc gene is amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product is subcloned into the Xba I and Cla I sites of pAd/CMV.1. The shuttle plasmid pAd.CMV. mutant IL-4.HFc is generated by cloning the PCR product encoding mutant IL-4 (Zurawski et al., (1993) Receptors for interleukin-13 and interleukin-4 are complex and share a novel component that functions in signal transduction. EMBO J. 12:2463–2670, lacking its termination codon and engineered with Eco RV and Xba I at its 5' and 3' ends respectively using primer sequences IL-4 forward 5'-TGTATGATATCATG GGTCTCAAC-CCCCAGCTAGTTGTC (SEQ ID NO:19) and IL-4 reverse 5'-TGTATFCTAGACGAGTAATCCATTTGCATGATGCT (SEQ ID NO:20), into the pAd.CMV.HFc construct in frame with HFc. In order to rescue a recombinant adenovirus, 10 μg of pAd.CMV. mutant IL4.HFc is cotransfected by calcium phosphate coprecipitation (Wigler et al., 1977) into 293 cells along with 5 μg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid is exceeded by approximately 2 kb (McGrory et al., 1988).

Homologous recombination then takes place in the 293 cells between the two plasmids replacing the E1 region and pBRX in JM17 with the cDNA from pAd.CMV. mutant IL-4:HFc. The resulting DNA can then be packaged into the adenovirus capsid and is also rendered replication-defective as a consequence of its lacking of the E1 region required for efficient replication. E1 is supplied in trans by the 293 cells. Single plaques of Ad5.hCMV. mutant IL-4:HFc are amplified in 293 cells from which crude viral lysate (CVL) was used for cell line transduction and the generation of serum-free conditioned medium.

ICAM-IgG:

An immunoadhesin comprising intercellular adhesion molecule-1 (ICAM) and the constant region of the murine IgGI heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATCCATGGAGCAGCACCAAGGTGGACA (SEQ ID NO:8) and HFc reverse 5'-TGTATATCGATCTGGGATCATTTACCAGGA (SEQ ID NO:9) engineered with Nco I and Cla I at its 5' and 3' ends respectively. The 1397 bp PCR product encoding the putative extracellular domain of ICAM-1 (Ballantyne, C. M., O'Brien, W. E., Beaudet, A. L. (1989) Nucleotide sequence of the cDNA for murine intercellular adhesion molecule-1 (ICAM-1). Nucleic Acids Research 17, 5853.), lacking its transmembrane domain and engineered with Eco RV and Nco I at its 5' and 3' ends respectively using primer sequences ICAM forward 5'-TGTATGATATCATGGAGCGAAGGTTAGTG (SEQ ID NO:21) and ICAM reverse 5'-TGTATCCATGGCCTGGCTTTAATTGTCATG (SEQ ID NO:22), into the pAd.CMV.HFc construct in frame with HFc. In order to rescue a recombinant adenovirus, 10 µg of pAd.CMV.ICAM.HFc was cotransfected by calcium phosphate coprecipitation (Wigler et al., 1977) into 293 cells along with 5 µg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid is exceeded by approximately 2 kb (McGrory et al., 1988).

Homologous recombination then takes place in the 293 cells between the two plasmids replacing the E1 region and pBRX in JM17 with the cDNA from pAd.CMV.ICAM:HFc. The resulting DNA was then packaged into the adenovirus capsid and was also rendered replication-defective as a consequence of its lacking of the E1 region required for efficient replication. E1 was supplied in trans by the 293 cells. Single plaques of Ad5.hCMV.ICAM:HFc were amplified in 293 cells from which crude viral lysate (CVL) was used for cell line transduction and the generation of serum-free conditioned medium.

IL-2-IgG:

An immunoadhesin comprising interleukin-2 and the constant region of the murine IgG1 heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV.1. The shuttle plasmid pAd.CMV.IL-2.HFc was generated by cloning the PCR product encoding IL-2 (IL-2) (Zurawski, G. (1989) Mouse interleukin-2structure-function studies: substitutions in the first alpha-helix can specifically inactivate p70 receptor binding and mutations in the fifth alpha helix can specifically inactivate p55 receptor binding. EMBO J 8, 2583–90), lacking its termination codon and engineered with Eco RV and Xba I at its 5' and 3' ends respectively using primer sequences IL-2 forward 5'-TGTATGATATCATG TACAGCACTGAGCTC (SEQ ID NO:16) and IL2 reverse 5'-TGTATTCTAGA TTGAGGGCTTGTTGAGATG (SEQ ID NO:17), into the pAd.CMV.HFc construct in frame with HFc. In order to rescue a recombinant adenovirus, 10 µg of pAd.CMV.IL-2.HFc was cotransfected by calcium phosphate coprecipitation (Wigler et al., 1977) into 293 cells along with 5 µg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid was exceeded by approximately 2 kb (McGrory et al., 1988).

Homologous recombination then takes place in the 293 cells between the two plasmids replacing the El region and pBRX in JM17 with the cDNA from pAd.CMV.IL-2:HFc. The resulting DNA was then packaged into the adenovirus capsid and was also rendered replication-defective as a consequence of its lacking of the E1 region required for efficient replication. E1 was supplied in trans by the 293 cells. Single plaques of Ad5.hCMV.IL-2:HFc were amplified in 293 cells from which crude viral lysate (CVL) was used for cell line transduction and the generation of serum-free conditioned medium.

TGF-β1-IgG:

An immunoadhesin comprising transforming growth factor β-1 and the constant region of the murine IgG1 heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 is constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTiGGGATCATTTACCAGGA (SEQ ID NO:9) engineered with Xba I and Cla I at its 5' and 3' ends respectively. The 718 base pair (bp) PCR product is subcloned into the Xba I and Cla I sites of pAd/CMV.1. The shuttle plasmid pAd.CMV.TGF-β1:HFc was generated by cloning the PCR product encoding transforming growth factor beta-1 (TGF-β1) (Roberts et al, 1988), lacking its termination codon and engineered with Eco RV and Xba I at its 5' and 3' ends respectively using primer sequences TGF-β1 forward 5=-TGTATGATATCATGCCGCCCTCCGGGCTG (SEQ ID NO:23) and TGF-β1 reverse 5'-TGTATTCTAGATCAGCTGCACTTGCAGGA (SEQ ID NO: 24), into the pAd. CMV.HFc construct in frame with HFc. In order to rescue a recombinant adenovirus, 10 μg of pAd.CMV.TGF-β1:HFc was cotransfected by calcium phosphate coprecipitation (Wigler et al., 1977) into 293 cells along with 5 μg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid was exceeded by approximately 2 kb (McGrory et al., 1988).

Homologous recombination then takes place in the 293 cells between the two plasmids replacing the E1 region and pBRX in JM17 with the cDNA from pAd5.hCMV.TGF-β1:HFc. The resulting DNA was then packaged into the adenovirus capsid and was also rendered replication-defective as a consequence of its lacking of the E1 region required for efficient replication. E1 was supplied in trans by the 293 cells. Single plaques of Ad5.hCMV.TGF-β1:HFc were amplified in 293 cells from which crude viral lysate (CVL) was used for cell line transduction and the generation of serum-free conditioned medium.

TGF-β1$^{223,225}$-IgG

An immunoadhesin comprising transforming growth factor beta-1$^{223,225}$ and the constant region of the murine IgG1 heavy chain was produced as follows. The plasmid pAd/CMV.1 containing the first 16 map units of the adenovirus genome with the region between map unit 1.3 and map unit 9.4 deleted and replaced by the cytomegalovirus major immediate early promoter/enhancer region from pCDNA3 (Invitrogen, San Diego, Calif.) into the adenovirus shuttle plasmid pAdeno-1 was constructed as described previously (Sullivan et al., 1996). The plasmid pAd/CMV.1 was then modified to contain the murine immunoglobulin gamma 1 heavy chain gene hinge, CH2, and CH3 domains (HFc). To engineer this construct, the HFc gene was amplified by the polymerase chain reaction (PCR) from the plasmid HFc-pUC18 using primer sequences HFc forward 5'-TGTATTCTAGAAGCAGCACCAAGGTGGACA (SEQ ID NO:8) and HFc reverse 5'-TGTATATCGATCTGGGATCATTTACCAGGA (SEQ ID NO:9) engineered with Xba I and Cla I at its 5' and 3' ends respectively. The 718 base pair (bp) PCR product was subcloned into the Xba I and Cla I sites of pAd/CMV.1. The shuttle plasmid pAd.CMV.TGF-β1$^{223,225}$:HFc was generated by cloning the PCR product encoding transforming growth factor beta-1$^{223,225}$ (TGF-β1$^{223,225}$) (Brunner, A. M. et al. 1989), lacking its termination codon and engineered with Eco RV and Xba I at its 5' and 3' ends respectively using primer sequences TGF-β1$^{223,225}$ forward 5'-TGTATGATATCATGCCGCCTTCGGGGCTGC (SEQ ID NO:25) and TGF-β1$^{223,225}$ reverse 5'-TGTATTCTAGAGCTGCACTTGCAGGAACGCAC (SEQ ID NO:26), into the pAd.CMV.HFc construct in frame with HFc. In order to rescue a recombinant adenovirus, 10 μg of pAd.CMV.TGF-β1$^{223,225}$:HFc is cotransfected by calcium phosphate coprecipitation (Wigler et al., 1977) into 293 cells along with 5 μg of the adenovirus type 5 genome containing plasmid pJM17 (supplied generously by Dr. Frank L. Graham, McMaster University, Hamilton, Ontario, Canada). pJM17 contains the full-length adenovirus type 5 genome and pBRX, a 4.3-kb insertion into the E1 region at 3.7 map units. Thus the maximum packaging limit of the cDNA into the virus capsid was exceeded by approximately 2 kb (McGrory et al., 1988).

Homologous recombination then takes place in the 293 cells between the two plasmids replacing the E1 region and pBRX in JM17 with the cDNA from pAd5.hCMV.TGF-β1$^{223,225}$:HFc. The resulting DNA was then packaged into the adenovirus capsid and was also rendered replication-defective as a consequence of its lacking of the E1 region required for efficient replication. E1 was supplied in trans by the 293 cells. Single plaques of Ad5.hCMV.TGF-β1$^{223,225}$:HFc were amplified in 293 cells from which crude viral lysate (CVL) was used for cell line transduction and the generation of serum-free conditioned medium.

Transduction of hRPE cells

Transductions of primary hRPE and other cell lines with Ad5.hCMV.mIL-10:HFc were performed in six well dishes ($1\times10^6$ cells/well) or when the cells were at confluence in 150 mm. dishes (Falcon, USA). All transductions were conducted at a multiplicity of infection (MOI) of 10. Cultures are incubated with CVL in medium containing 2% serum in a 5% $CO_2$ humidified incubator at 37° C. At ninety minutes following transduction an equivalent amount of serum containing medium are added. At twenty four hours, the medium is replaced with fresh complete medium and changed every other day until 24 hours before the culture supernatant was harvested at which time serum free medium was applied to the culture. Harvested supernatants are then centrifuged (2000×g) for 20 minutes to pellet any cellular debris and filtered through a 0.45 μM filter. Conditioned medium was then used immediately or frozen on dry ice and stored at −80° C. until used.

Immunoadhesin Isolation mIL-10:HFc was purified from serum-free culture supernatant to greater than 90% homogeneity by affinity chromatography on protein A sepharose CL-4B (Pharmacia, Uppsala, Sweden). mIL-10:HFc is eluted with 0.1M sodium citrate, pH 2.7, and neutralized immediately with 0.08 volume of 1M Tris. HCI (pH 9.0). Antibody-sandwich enzyme linked immunosorbant assay (ELISA) was used to screen cell culture supernatant. Polyvinyl chloride plates (Falcon) are coated for 60 minutes at 37° C. with goat anti-mouse IgGI (0.4 mg/ml, Boehringer Mannheim Corporation) diluted 1:100 in PBS/0.02% thimerosal. Plates were blocked with a solution containing 5% milk, 0.01% Tween-20®, and 0.05% methiolate for 60 minutes at 37° C. One hundred microliters of culture supernatant was incubated for 60 minutes at 37° C. Plates are washed five times with PBS/Tween 20® 0.01% and dried. The plates were then incubated with alkaline phosphatase conjugated anti-mouse IgG1, 1:2500 (TAGO, Inc., Burlingame, Calif.) at 37° C. for 60 minutes. Plates were washed and dried and 100 μl of substrate, 2 mg/ml p-nitrophenyl phosphate (Fluka, Switzerland) in 0.1M sodium carbonate buffer, pH 9.8 is added. The plates were incubated for 15–45 minutes and the OD read at 405 nm. Standard curves were generated using purified murine IgGI monoclonal antibody, B-Z1 (Biosource International, Camarillo, Calif.).

Assay for Effects of IL-10-IgG

The ability of mIL-10:HFc to induce a growth signal in the murine cell line, BaMR29a1, transfected with the murine IL-10 receptor was assessed in vitro. RPMI-1640 supplemented with 10% fetal bovine serum and 50 μM 2-mercaptoethanol (R/10/2) was used for dilution of cells as well as test samples. Cells were washed at least three times in R/10/2 to remove IL-3. Five thousand cells were incubated in the presence of either recombinant murine IL-10 or mL-10:HFc alone or in combination with one of the following: 2A5, an anti-murine IL-10 monoclonal antibody (Pharmingen, San Diego, Calif.); NIH 44-1, a monoclonal IgG1 mouse anti-human CD44 (a generous gift of Dr. Steven Shaw, National Cancer Institute, Bethesda, Md.), is used as an isotype control. Cultures were pulsed 48 hours later with 1 μCi/well of [$^3$H]thymidine for 16–18 hours. Cells were then harvested and [$^3$H]thymidine uptake was measured by liquid scintillation spectroscopy.

Transduction of Other Cell Lines

The ability of Ad5.hCMV.mIL-10:HFc to transduce other cell lines was assessed. Specifically, 293 cells (a human embryonic kidney cell line), C9 cells (a transformed Chinese hamster ovary cell line), and ARPE-19 cells (a cell line derived from human retinal pigment epithelial cells) were transduced at an MOI of 10 after seeding $1 \times 10^6$ cells/well in six well dishes twelve to sixteen hours prior to transduction. Serum-free conditioned medium from transduced cultures was examined for the presence of mIL-10:HFc by ELISA on days 2, 3, 5, and 7.

Characterization of murine IL-10-IgG mIL-10:HFc created by an in frame fusion of the complementary DNA molecules encoding murine IL-10 lacked its termination codon with the hinge and constant regions (CH2 and CH3 domains) of murine IgGI heavy chain. Rescue of the replication defective Ad5.hCMV.mIL-10:HFc was achieved by cotransfection of pAd.CMV.mIL-10.HFc with pJM17 (FIG. 1). Individual plaques were expanded in 293 cells and CVL then used to transduce cell lines for production of the secreted molecule. Affinity chromatography on immobilized protein A sepharose was used to bind the Fc domain of the immunoglobulin moiety and purify mIL-10:HFc from serum-free cell culture supernatants. One hundred milliliters of conditioned medium was used per milliliter of immobilized protein A. Yields of purified protein recovered from the peak fractions collected were typically in the range of 1.6–1.7 mg/liter of conditioned medium obtained from HRPE three days following transduction.

The subunit structure of mIL-10:HFc was examined by SDS-polyacrylamide gel electrophoresis. Under reducing conditions, an apparent molecular mass of ~52 kDa was observed. Under non reducing conditions, the observed species was twice that seen under reducing conditions, suggesting that mIL-10:HFc is a homodimer. Western blot analysis under non reducing conditions demonstrated reactivity of mIL-10:HFc with antibody to murine IgG. These results demonstrate mIL-10:HFc is a covalent homodimeric structure containing an antibody Fc binding domain.

Figure 2:
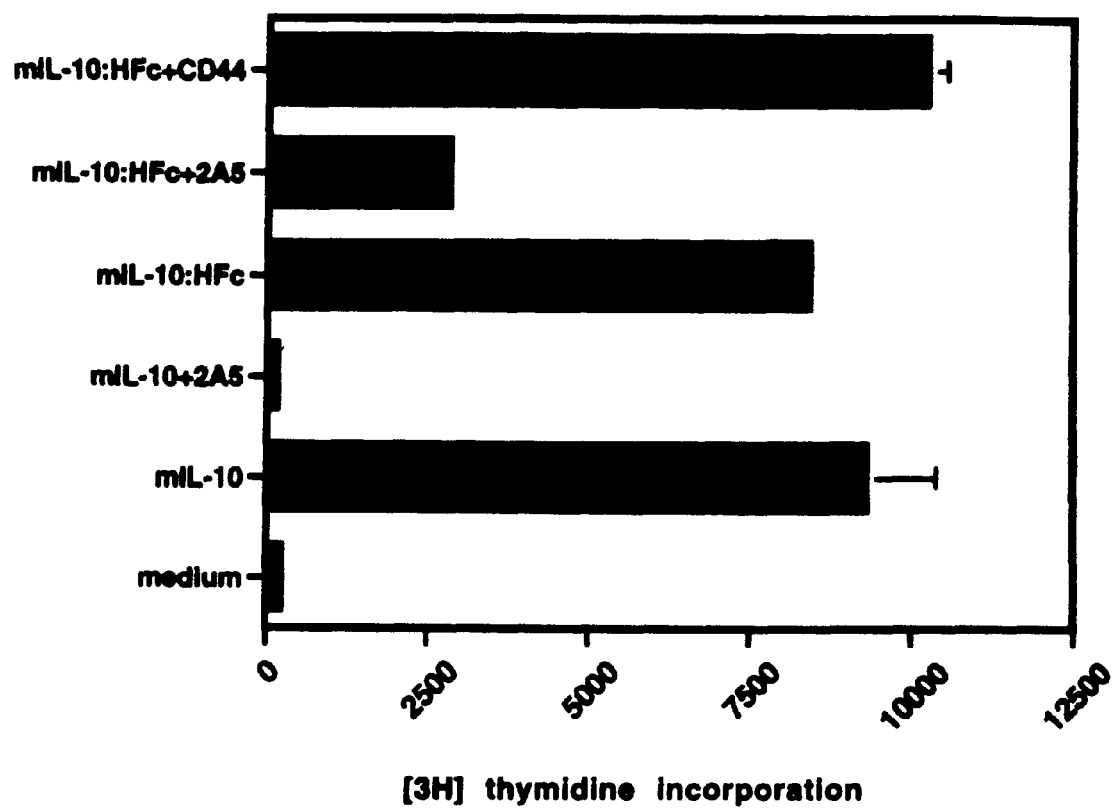
FIG. 2 shows the response of murine IL-10 receptor transfected cell line. BaMR29a1 to mIL-10 or mIL-10:HFc as measured by [$^3$H]thymidine incorporation. BaMR29a1 cells (5×10$^4$ cells/ml) were cultured in either 0.1 nM mIL-10 or 0.1 nM mIL-10:HFc for 48 hours and then pulsed with [$^3$H]thymidine for 16–18 hours. Responses in the presence of 10 μg of anti-mIL-10 per ml (2A5) or isotype control (CD44) mAb are shown. Error bars indicate the standard error of the mean of triplicate samples. In some examples, error bars are too small to be visualized.

To demonstrate that the immunoadhesin mIL-10:HFc is biologically active, BaMR29a1, an IL-3 dependent cell line transfected with the murine IL-10 receptor, was incubated with either 0.1 nM mIL-10:HFc or 0.1 nM recombinant murine IL-10 in the presence or absence of a neutralizing monoclonal antibody to murine IL-10, 2A5 or a monoclonal isotype control antibody, NIH 44-1. BaMR29a1 cells responded to both mIL-10 and mIL-10:HFc as assessed by [$^3$H]thymidine incorporation (FIG. 2). Inhibition by an anti-murine IL-10 antibody and the absence of inhibition with a murine IgG1 isotype control antibody shows an IL-10 specific mitogenic response.

Figure 3:
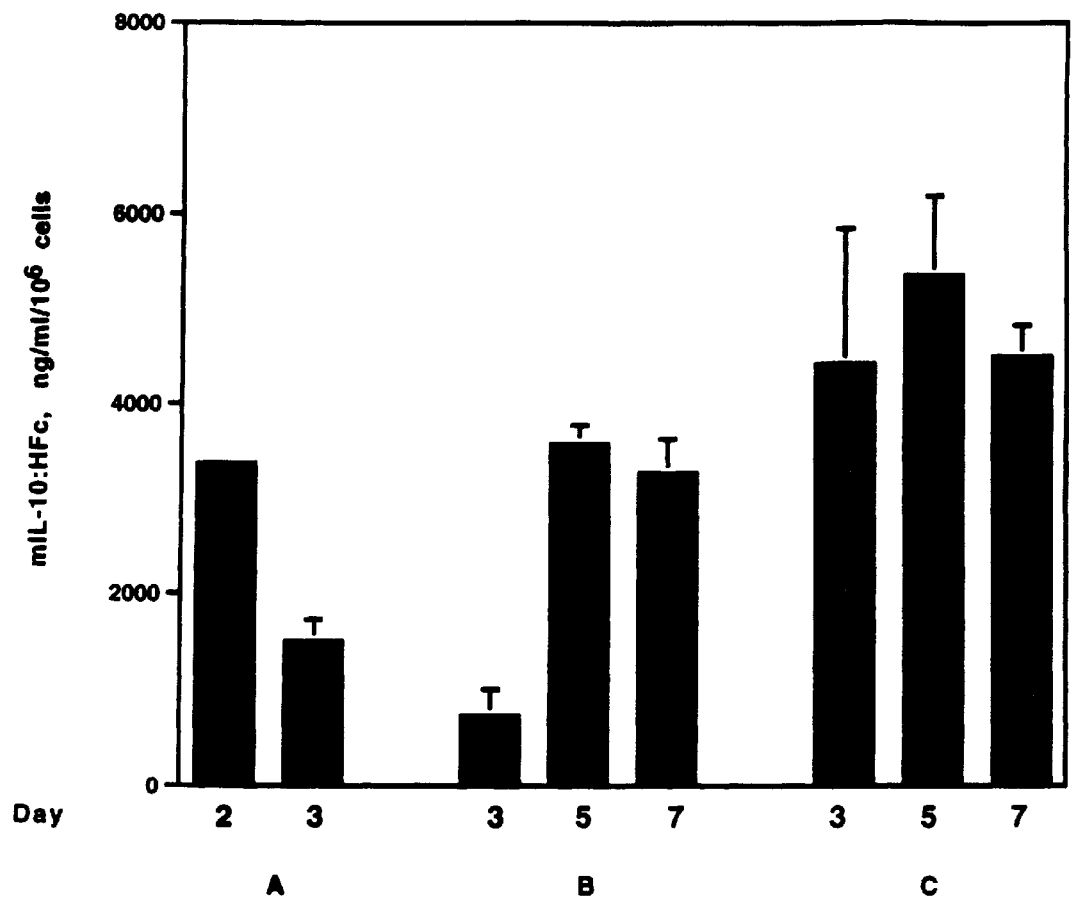
FIG. 3 shows the time course of expression in cell lines transduced with adenovirus vector Ad.CMV.mIL-10:HFc as measured by ELISA. 293 cells (A), C9 cells (B), or ARPE-19 cells (C) were plated in 6-well dishes at 1×10$^6$ cells/well 12–16 hours prior to transduction with Ad.CMV.mIL-10:HFc. Cells were fed every other day until one day prior to harvesting when complete medium was replaced with serum-free medium and conditioned for 24 hours. Time points indicated represent the mean of three experiments performed in triplicate. Error bars represent the standard error of the mean. In some examples, error bars are too small to be visualized. The nucleic acid sequences GATATCATGCCTGGC, ATGAAAAGCTCTAGA, TCTAGAAGCAGCACC, and GGTAAATGATCCCAGATCGAT, and the amino acid sequences Ala-Ile-Met-Pro-Cys, Met-Lys-Ser-Ser-Arg, and Ser-Arg-Ser-Ser-Thr are set forth in the Sequence Listing as SEQ ID NO:1, SEQ ID NO:2, SEQ ID NO:3, SEQ ID NO:4, SEQ ID NO:5, SEQ ID NO:6, and SEQ ID NO:7, respectfully.

Transduction of established cell lines by Ad5.hCMV.mIL-10:HFc was examined by ELISA. Serum-free culture supernatants conditioned for 24 hours derived from three cell lines at varying time points was analyzed. As shown in FIG. 3, transduction of all cell lines tested resulted in the production of detectable mIL-10:HFc, though to different degrees. The transformed human embryonic kidney cell line 293 resulted in mean values of 3380±75 and 1507±224 ng/ml at days 2 and 3 respectively. Ad5.hCMV.mIL-10:HFc transduced C9 cells yielded 743±263, 3580±197, and 3279±350 ng/ml of mIL-10:HFc at days 3, 5, and 7. ARPE-19 cells transduced with Ad5.hCMV.mIL-10:HFc resulted in 4426±1425, 5367±818, and 4500±330 ng/ml of mIL-10:HFc obtained at days 3, 5, and 7 respectively. No signal was detectable by ELISA in any cell line tested using serum-free conditioned medium from either untransduced cells or cells transduced with an E1-deleted adenovirus vector lacking a transgene.

The method described here demonstrates the first use of a replication-defective adenoviral vector for the production of an interleukin-10 immunoadhesin. It is a relatively simple and efficient means to produce recombinant immunoglobulins which can then be screened with regard to structure and bioactivity. Due to the efficient nature of adenoviral transduction, virtually every cell in a tissue culture dish contains the transgene of interest. We have demonstrated >95% transduction of primary human RPE at an MOI of 10 pfu/cell in culture (Sullivan et al., 1996). As a consequence of its high transduction efficiency, the need for selection of transduced cells is obviated as the level of recombinant protein expression can be correlated directly with the multiplicity of infection. This is supported further by the demonstration at three days of increased amounts of mIL-10:HFc contained in serum-free conditioned medium obtained from ARPE-19 cells transduced with Ad5.hCMV.mIL-10:HFc (Levrero et al., 1991). (Zheng et al. "Administration of Noncytolytic IL-10/Fc in Murine Models of Lipopolysaccharide-induced Septic Shock and Allogeneic Islet Transplantation" J. Immunol. 154:5590–6000).

As transgene expression occurs in eukaryotic cells, appropriate posttranslational modification is more likely to take place than in insect or prokaryotic cells. The use of a replication defective adenoviral vector for interleukin-10 immunoadhesin production is further underscored by demonstration of a growth response which is blocked specifically by an anti-mIL-10 monoclonal antibody in a mitogenic assay using the recombinant murine interleukin-10 receptor positive cell line BaMR29a1. The structure of mIL-10:HFc also confers the homodimeric state of native mIL-10 in solution. In addition to being expressed as a homodimer, such a construct will also possess the property of an increased serum half-life.

Treatment of uveitis

The immunoadhesins produced by the methods described herein provide necessary reagents for treatment of various conditions, such as uveitis. Experimental autoimmune uveoretinitis (EAU) and endotoxin-induced uveitis (EIU) in rodents produced by immunization with retinal antigens and lipopolysaccharide respectively, serve as models for human uveitis. Study of the disease process requires the use of a living organism containing the organ system of interest, i.e. the visual sense organs. EAU and EIU models exist in a number of animals including rabbits, guinea pigs, rats, and mice. Many features of the disease spectrum are present in these models and the murine model of uveitis is particularly useful for the study of the immunologic mechanisms of the disease. First, numerous strains of genetically defined mice are available. Second, recombinant cytokines and antibodies to cell surface markers for use in the mouse are widely available. Finally, of those available models, the murine model possesses numerous clinical and pathological similarities to the human disease which make it an especially suitable organism for this protocol. The studies undertaken with this model are fundamental to an increased understanding of the pathogenesis of this disease and the development of a novel approach to the treatment of uveitis in humans. The following exemplifies various considerations which one skilled in the art will recognize as experimental parameters which are typical and routine for use of the mouse as a model for human therapy. The methods are readily adapted for human administration. (Mochizuki et al. "Effects of Cyclosporine and Other Immunosuppressive Drugs on Experimental Autoimmune Uveoretinitis in Rats" Invest. Ophthalmol. Vis. Sci. 26:226–32 (1988)).

EIU induction by endotoxin: Adult mice can be injected in one hind footpad with 200 $\mu$g of Salmonella typhimurium endotoxin in a volume of 0.1 ml of sterile saline solution. Aseptic technique should be used throughout the procedure. The animals should be monitored daily for signs of pain and discomfort (e.g. ruffled fur, huddling), and given an analgesic when appropriate.

EAU induction by active immunization: Adult mice are immunized with retinal antigens (IRBP, S-antigen, or peptide fragments derived from either) emulsified in complete Freund's adjuvant. A volume of 0.1–0.2 ml of emulsified antigen can be administered in a subcutaneous fashion (divided between up to three sites) utilizing a 25 gauge needle. As an additional adjuvant, Bordetella pertussis toxin can be administered intraperitoneally (up to 1 $\mu$g/animal in 0.2 ml PBS or RPMI). Aseptic technique should be used throughout the procedure.

EAU induction by adoptive transfer of immune cells: Experiments may require the injection of immune competent cells (up to 20 million) from genetically compatible donors. This can be achieved by means of an aseptic injection of cells by either the intravenous or intraperitoneal route. Cells (0.2 to 1 million) may also be administered via an intraocular route with a Hamilton syringe and 33 gauge needle in a total volume of 10 $\mu$l. This maneuver can be performed under general anesthesia with the aid of a binocular microscope. Intraocular injections are routinely undertaken in human patients with little or no anesthesia for the procedure, and do not require analgesia after the procedure.

Immunomodulation of EAU and EIU: Mice immunized with antigen or injected with endotoxin can be treated for various periods of time with an immunomodulatory agent. Administration can be via injection either intravenously, intraperitoneally, or intraocularly. Intraocular administration can be by means of a Hamilton syringe utilizing a 33 gauge needle. This procedure can be performed with the assistance of binocular microscope under general anesthesia under aseptic conditions. Intraocular injections are routinely undertaken in human patients with little or no anesthesia for the procedure, and do not require analgesia after the procedure. Intraocularly injected animals should be inspected daily for the presence of discomfort (e.g. tearing, eye rubbing, guarding).

The treatment modality involves the use of an immunoadhesin (IA) which are important in the treatment of human diseases and conditions. For exam le, the immunoadhesin CD4-IgG has been used in a human clinical trial. (Hodges et al. "Phase 1 Study of Recombinant Human CD4-Immunoglobulin G Therapy of Patients with AIDS and AIDS-related Complex" Antimicrob. Agents Chemother. 35:2580–6 (1991)). In those studies using animals, no toxicity or adverse effects have been described and minimal immunogenicity has been reported. Various IA's which can be evaluated include: viral IL-10, murine IL-10, murine ICAM-1, murine IL-2 (and a mutant form of IL-2 capable of binding the IL-2 receptor without activation of the receptor), murine IL-1 receptor antagonist, transforming growth factor beta-1, and IL-4 (and a mutant form of IL-4 capable of binding the IL-4 receptor without its activation). Each of these agents may used alone or in combination. Additionally, a control comprised of a secreted form of the antibody constant region lacking a binding region can be used.

Treatment Using Adenovirus

Recombinant adenovirus particles carrying a nucleic acid encoding an immunoadhesin can be administered, such as intramuscularly or intravenously. A typical dose can be that amount typical for related adenovirus administrations, such as $1\times10^2$–$1\times10^{12}$ plaque-forming units of adenovirus. For administration of recombinant immunoadhesin, the dose may range from 0.001–10 mg/kg.

Monitoring of EAU and EIU: Evaluation of disease progression should be performed once or twice weekly by observation of the anterior and posterior segments in EIU and the posterior segment in EAU. The posterior segment should be examined following pupillary dilation with a mydriatic and/or dilating agent (e.g. tropicamide 1% and phenylephrine 2.5%). Inspection of either the anterior or posterior segments can be undertaken with an operating microscope. In addition, fluorescein angiography may be performed to evaluate the presence of vascular leakage. In this instance, the animal can be anesthetized and its pupils dilated as in evaluation of the posterior segment. In this example, the animal will receive an intravenous injection of a clinical fluorescein solution (0.1 ml of a 1:10 dilution in PBS) immediately followed by photography of the fundus vasculature with camera equipped with appropriate filters for angiography. This procedure is performed safely and routinely in humans (who do not require general anesthesia). In the EAU, assessment of cellular immunity to the administered antigen may be by delayed hypersensitivity. 20 $\mu$g of antigen in 20 $\mu$l can be injected subcutaneously into the pinna of one ear while the other ear receives saline) under anesthesia. Ear swelling can measured with a micrometer 24 to 48 hours later.

Collection of blood and tissue in EAU: Two weeks to 3 months after immunization the animals may be sacrificed by $CO_2$ inhalation and the eyes and or lymphoid organs will be removed. When serum is required for analysis, animals under deep $CO_2$ anesthesia can be bled by cardiac puncture immediately preceding the euthanasia. For some experiments, it may be necessary to confirm that an immune response has occurred prior to sacrifice of the animal. Therefore, blood samples can be drawn from the orbital plexus at weekly intervals. The plexus may be entered with a short-beveled 25-gauge needle and two drops of blood will be collected under general anesthesia. This procedure is relatively straightforward and can be performed with minimal trauma to the animal.

Collection of blood and tissue in EIU: 0–72 hours following injection of endotoxin the animals may be sacrificed by $CO_2$ inhalation and the eyes can be removed. When serum is required for analysis, animals under deep $CO_2$ anesthesia may be bled by cardiac puncture immediately preceding the euthanasia.

It is well known in the art that the rodent model is applicable to humans. It is also well known in the art that the use of the murine model to evaluate immunoadhesins and cellular responses to immunoadhesins is also applicable to humans. The methods provided herein are also applicable to humans. The present invention therefore also provides for non-murine counterparts or homologs for the immunoadhesins and other compounds provided herein, as well as the use of the methods provided herein with non-murine immunoadhesins, particularly immunoadhesins in the context of an adenoviral genome.

It will be apparent to one skilled in the art that non-murine homologs of the murine immunoadhesins provided herein can be constructed. For example, using available sequence databases such as GenBank, one can construct human homologs to the murine immunoadhesins provided herein using the sequence information from the database in combination with the present disclosure. Other methods of constructing non-murine, particularly human, homologs of the immunoadhesin provided herein will be apparent to one skilled in the art as discussed above.

References

Aruffo, A., Stamenkovic, I., Melnick, M., Underhill, C. B. and Seed, B. (1990) CD44 is the principal cell surface receptor for hyaluronate. Cell 61(7), 1303–13.

Ashkenazi, A., Capon, D. J. and Ward, R. H. (1993) Immunoadhesins. Int Rev Immunol 10(2-3), 219–27.

Ashkenazi, A., Marsters, S. A., Capon, D. J., Chamow, S. M., Figari, I. S., Pennica, D., Goeddel, D. V., Palladino, M. A. and Smith, D. H. (1991) Protection against endotoxic shock by a tumor necrosis factor receptor immunoadhesin. Proc Natl Acad Sci USA 88(23), 10535–9.

Ballay, A., Levrero, M., Buendia, M. A., Tiollais, P. and Perricaudet, M. (1985) In vitro and in vivo synthesis of the hepatitis B virus surface antigen and of the receptor for polymerized human serum albumin from recombinant human adenoviruses. Embo J 4(13B), 3861–5.

Beck, J. T., Marsters, S. A., Harris, R. J., Carter, P., Ashkenazi, A. and Chamow, S. M. (1994) Generation of soluble interleukin-1 receptor from an immunoadhesin by specific cleavage. Mol Immunol 31(17), 1335–44.

Byrn, R. A., Mordenti, J., Lucas, C., Smith, D., Marsters, S. A., Johnson, J. S., Cossum, P., Chamow, S. M., Wurm, F. M., Gregory, T. and et al. (1990) Biological properties of a CD4 immunoadhesin. Nature 344(6267), 667–70.

Capon, D. J., Chamow, S. M., Mordenti, J, Marsters, S. A., Gregory, T., Mitsuya, H., Byrn, R. A., Lucas, C., Wurm, F. M., Groopman, J. E. and et al. (1989) Designing CD4 immunoadhesins for AIDS therapy. Nature 337(6207), 525–31.

Chamow, S. M., Duliege, A. M., Ammann, A., Kahn, J. O., Allen, J. D., Eichberg, J. W., Byrn, R. A., Capon, D. J., Ward, R. H. and Ashkenazi, A. (1992) CD4 immunoadhesins in anti-HIV therapy: new developments. Int J Cancer Suppl 7, 69–72.

Cheon, H. G., LaRochelle, W. J., Bottaro, D. P., Burgess, W. H. and Aaronson, S. A. (1994) High-affinity binding sites for related fibroblast growth factor ligands reside within different receptor immunoglobulin-like domains. Proc Natl Acad Sci USA 91(3), 989–93.

de WaalMalefyt, R., Yssel, H., Roncarolo, M. G., Spits, H. andde Vries, J. E. (1992) Interleukin-10. Curr Opin Immunol 4(3), 314–20.

Dunn, K. C., Aotaki, K. A., Putkey, F. R. and Hjelmeland, L. M. (1996) ARPE-19, a human retinal pigment epithelial cell line with differentiated properties. Exp Eye Res 62(2), 155–69.

Finck, B. K, Linsley, P. S. and Wofsy, D. (1994) Treatment of murine lupus with CTLA4Ig. Science 265(5176), 1225–7.

Graham, F. L. and Prevec, L. (1991) Manipulation of adenovirus vectors. In: E. J. Murray (Ed), Gene transfer and Expression Protocols. Methods in Molecular Biology, Vol. 7, The Humana Press Inc., Clifton, N.J., pp. 109–128.

Haak-Frendscho, M., Ridgway, J., Shields, R., Robbins, K., Gorman, C. and Jardieu, P. (1993) Human IgE receptor alpha-chain IgG chimera blocks passive cutaneous anaphylaxis reaction in vivo. J Immunol 151(1), 351–8.

Heidaran, M. A., Mahadevan, D. and Larochelle, W. J. (1995) Beta PDGFR-IgG chimera demonstrates that human beta PDGFR Ig-like domains 1 to 3 are sufficient for high affinity PDGF BB binding. Faseb J 9(1), 140–5.

Ho, A. S., Liu, Y, Khan, T. A., Hsu, D. H., Bazan, J. F. and Moore, K. W. (1993) A receptor for interleukin 10 is related to interferon receptors. Proc Natl Acad Sci USA 90(23), 11267–71.

Jin, H., Yang, R., Marsters, S. A., Bunting, S. A., Wurm, F. M., Chamow, S. M. and Ashkenazi, A. (1994) Protection against rat endotoxic shock by p55 tumor necrosis factor (TNF) receptor immunoadhesin: comparison with anti-TNF monoclonal antibody. J Infect Dis 170(5), 1323–6.

Lamarche, N., Massie, B., Richer, M., Paradis, H. and Langelier, Y. (1990) High level expression in 293 cells of the herpes simplex virus type 2 ribonucleotide reductase subunit 2 using an adenovirus vector. J Gen Virol 71(Pt 8), 1785–92.

LaRochelle, W. J., Dirsch, O. R., Finch, P. W., Cheon, H. G., May, M., Marchese, C., Pierce, J. H. and Aaronson, S. A. (1995) Specific receptor detection by a functional keratinocyte growth factor-immunoglobulin chimera. J Cell Biol 129(2), 357–66.

Lenschow, D. J., Zeng, Y, Thistlethwaite, J. R., Montag, A., Brady, W., Gibson, M. G., Linsley, P. S. and Bluestone, J. A. (1992) Long-term survival of xenogeneic pancreatic islet grafts induced by CTLA4Ig. Science 257(5071), 789–92.

Levrero, M., Barban, V., Manteca, S., Ballay, A., Balsamo, C., Avantaggiati, M. L., Natoli, G., Skellekens, H., Tiollais, P. and Perricaudet, M. (1991) Defective and non-defective adenovirus vectors for expressing foreign genes in vitro and in vivo. Gene 101(2), 195–202.

Lin, H., Bolling, S. F., Linsley, P. S., Wei, R. Q., Gordon, D., Thompson, C. B. and Turka, L. A. (1993) Long-term acceptance of major histocompatibility complex mismatched cardiac allografts induced by CTLA4Ig plus donor-specific transfusion. J Exp Med 178(5), 1801–6.

Linsley, P. S., Brady, W, Grosmaire, L., Aruffo, A., Damle, N. K. and Ledbetter, J. A. (1991) Binding of the B cell activation antigen B7 to CD28 costimulates T cell proliferation and interleukin 2 mRNA accumulation. J Exp Med 173(3), 721–30.

Linsley, P. S. and Ledbetter, J. A. (1993) The role of the CD28 receptor during T cell responses to antigen. Annu Rev Immunol 11 (191), 191–212.

McGrory, W. J., Bautista, D. S. and Graham, F. L. (1988) A simple technique for the rescue of early region I mutations into infectious human adenovirus type 5. Virology 163(2), 614–7.

Moore, K. W., Vieira, P., Fiorentino, D. F., Trounstine, M. L., Khan, T. A. and Mosmann, T. R. (1990) Homology of cytokine synthesis inhibitory factor (IL-10) to the Epstein-Barr virus gene BCRFI [published erratum appears in Science Oct. 26, 1990;250(4980):494]. Science 248(4960), 1230–4.

Sullivan, D. M., Chung, D. C., Anglade, E., Nussenblatt, R. B. and Csaky, K. C. (1996) Adenovirus mediated gene transfer of ornithine aminotransferase in cultured human RPE. Invest Ophthalmol Vis Sci 37(5), 768–74.

Wallace, P. M., Johnson, J. S., MacMaster, J. F., Kennedy, K. A., Gladstone, P. and Linsley, P. S. (1994) CTLA4Ig treatment ameliorates the lethality of murine graft-versus-host disease across major histocompatibility complex barriers. Transplantation 58(5), 602–10.

Watson, S. R., Imai, Y., Fennie, C., Geoffroy, J. S., Rosen, S. D. and Lasky, L. A. (1990) A homing receptor-IgG chimera as a probe for adhesive ligands of lymph node high endothelial venules. J Cell Biol 110(6), 2221–9.

Wigler, M., Silverstein, S., Lee, L. S., Pellicer, A., Cheng, Y. c. and Axel, R. (1 977) Transfer of purified herpes virus thymidine kinase gene to cultured mouse cells. Cell 11(1), 223–32.

Zheng, X. X., Steele, A. W., Nickerson, P. W., Steurer, W., Steiger, J. and Strom, T. B. (1995) Administration of non-cytolytic IL-10/Fc in murine models of lipopolysaccharide-induced septic shock and allogeneic islet transplantation. J Immunol 154(10), 5590–600.

What is claimed is:

1. A compound comprising a recombinant nucleic acid encoding an immunoadhesin comprising vIL-10-IgG inserted within an adenoviral nucleic acid, wherein the recombinant nucleic acid can be packaged in an adenovirus particle and wherein expression of the recombinant nucleic acid encoding the immunoadhesin results in production of the immunoadhesin protein.

2. The compound of claim 1, wherein the recombinant nucleic acid is replication deficient.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:1:

GATATCATGC CTGGC                                                15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:2:

ATGAAAAGCT CTAGA                                                15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:3:

TCTAGAAGCA GCACC                                               15

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:4:

```
GGTAAATGAT CCCAGATCGA T                                          21

(2) INFORMATION FOR SEQ ID NO:5:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:5:

Ala Ile Met Pro Cys
1               5

(2) INFORMATION FOR SEQ ID NO:6:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:6:

Met Lys Ser Ser Arg
1               5

(2) INFORMATION FOR SEQ ID NO:7:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:7:

Ser Arg Ser Ser Thr
1               5

(2) INFORMATION FOR SEQ ID NO:8:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: oligonucleotide (xi) SEQUENCE DESCRIPTION: SEQ ID NO:8:

TGTATTCTAG AAGCAGCACC AAGGTGGACA                                 30

(2) INFORMATION FOR SEQ ID NO:9:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: oligonucleotide (xi) SEQUENCE DESCRIPTION: SEQ ID NO:9:

TGTATATCGA TCTGGGATCA TTTACCAGGA                                 30
```

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

```
TGTATGATAT CATGCCTGGC TCAGCACTG                          29
```

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

```
TGTATTCTAG AGCTTTTCAT TTTGATCATC AT                      32
```

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

```
TGTATGATAT CATGGAGCGA AGGTTAGTG                          29
```

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

```
TGTATTCTAG ACCTGGCTTT AATTGTCATG                         30
```

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

```
TGTATGATAT CATGGCGCTC TGGGTGACT                          29
```

(2) INFORMATION FOR SEQ ID NO:15:

(i) SEQUENCE CHARACTERISTICS:
        (A) LENGTH: 28 base pairs

```
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:15:

TGTATTCTAG AGAAGGGGCC GTGGCGAA                                             28

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:16:

TGTATGATAT CATGTACAGC ACTGAGCTC                                            29

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:17:

TGTATTCTAG ATTGAGGGCT TGTTGAGATG                                           30

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:18:

TGTATAAGCT TATGGAGCGA AGGTTAGTG                                            29

(2) INFORMATION FOR SEQ ID NO:19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:19:

TGTATGATAT CATGGGTCTC AACCCCCAGC TAGTTGTC                                  38

(2) INFORMATION FOR SEQ ID NO:20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE:  oligonucleotide
```

(xi) SEQUENCE DESCRIPTION: SEQ ID NO:20:

TGTATTCTAG ACGAGTAATC CATTTGCATG ATGCT                35

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:21:

TGTATGATAT CATGGAGCGA AGGTTAGTG                       29

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:22:

TGTATCCATG GCCTGGCTTT AATTGTCATG                      30

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:23:

TGTATGATAT CATGCCGCCC TCCGGGCTG                       29

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:24:

TGTATTCTAG ATCAGCTGCA CTTGCAGGA                       29

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE:  oligonucleotide (xi) SEQUENCE DESCRIPTION: SEQ ID NO:25:

TGTATGATAT CATGCCGCCT TCGGGGCTGC                      30

(2) INFORMATION FOR SEQ ID NO:26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:26:

TGTATTCTAG AGCTGCACTT GCAGGAACGC AC      32